US008447379B2

(12) United States Patent
Flynn

(10) Patent No.: US 8,447,379 B2
(45) Date of Patent: *May 21, 2013

(54) DETECTION, MEASUREMENT, AND IMAGING OF CELLS SUCH AS CANCER AND OTHER BIOLOGIC SUBSTANCES USING TARGETED NANOPARTICLES AND MAGNETIC PROPERTIES THEREOF

(75) Inventor: Edward R Flynn, Albuquerque, NM (US)

(73) Assignee: Senior Scientific, LLC, Albuquerque, NM (US)

( * ) Notice: Subject to any disclaimer, the term of this patent is extended or adjusted under 35 U.S.C. 154(b) by 89 days.

This patent is subject to a terminal disclaimer.

(21) Appl. No.: 13/249,994

(22) Filed: Sep. 30, 2011

(65) Prior Publication Data
US 2012/0035458 A1 Feb. 9, 2012

Related U.S. Application Data

(63) Continuation-in-part of application No. 11/940,673, filed on Nov. 15, 2007, now Pat. No. 8,060,179, and a continuation-in-part of application No. 12/337,554, filed on Dec. 17, 2008, now Pat. No. 8,118,754, which is a continuation-in-part of application No. 11/957,988, filed on Dec. 17, 2007, now abandoned, which is a continuation-in-part of application No.

(Continued)

(51) Int. Cl.
*A61B 5/05* (2006.01)
(52) U.S. Cl.
USPC ........................................................ 600/409
(58) Field of Classification Search
None
See application file for complete search history.

(56) References Cited

U.S. PATENT DOCUMENTS

| 3,741,198 A | 6/1973 | Burton |
| 4,018,886 A | 4/1977 | Giaever |

(Continued)

FOREIGN PATENT DOCUMENTS

| WO | WO01/74374 | 10/2001 |
| WO | WO2005/059118 | 6/2005 |

(Continued)

OTHER PUBLICATIONS

Adolphi et al., Characterization of magnetite nanoparticles for SQUID-relaxometry and magnetic needle biopsy, Feb. 20, 2009, Journal of Magnetism and Magnetic Materials, vol. 321, ls. 10, p. 1459-1464.

(Continued)

*Primary Examiner* — Jacqueline Cheng
(74) *Attorney, Agent, or Firm* — V. Gerald Grafe

(57) ABSTRACT

The present invention can provide a method of determining the presence, location, quantity, or a combination thereof, of a biological substance, comprising: (a) exposing a sample to a plurality of targeted nanoparticles, where each targeted nanoparticle comprises a paramagnetic nanoparticle conjugated with one or more targeting agents that preferentially bind with the biological substance, under conditions that facilitate binding of the targeting agent to at least one of the one or more biological substances; (b) subjecting the sample to a magnetic field of sufficient strength to induce magnetization of the nanoparticles; (c) measuring a magnetic field of the sample after decreasing the magnetic field applied in step b below a threshold; (d) determining the presence, location, quantity, or a combination thereof, of the one or more biologic substances from the magnetic field measured in step (c).

19 Claims, 17 Drawing Sheets

Related U.S. Application Data

11/940,673, filed on Nov. 15, 2007, now Pat. No. 8,060,179, application No. 13/249,994, which is a continuation-in-part of application No. PCT/US2010/051417, filed on Oct. 5, 2010, which is a continuation-in-part of application No. PCT/US2010/055729, filed on Nov. 5, 2010, which is a continuation-in-part of application No. PCT/US2011/028746, filed on Mar. 16, 2011.

(60) Provisional application No. 61/386,961, filed on Sep. 27, 2010, provisional application No. 61/389,233, filed on Oct. 3, 2010, provisional application No. 60/866,095, filed on Nov. 16, 2006, provisional application No. 61/248,775, filed on Oct. 5, 2009, provisional application No. 61/329,076, filed on Apr. 28, 2010, provisional application No. 61/377,854, filed on Aug. 27, 2010, provisional application No. 61/314,392, filed on Mar. 16, 2010, provisional application No. 61/331,816, filed on May 5, 2010, provisional application No. 61/361,998, filed on Jul. 7, 2010, provisional application No. 61/259,011, filed on Nov. 6, 2009, provisional application No. 61/308,897, filed on Feb. 27, 2010, provisional application No. 61/310,700, filed on Mar. 4, 2010, provisional application No. 61/314,370, filed on Mar. 16, 2010, provisional application No. 61/454,560, filed on Mar. 20, 2011.

(56) References Cited

U.S. PATENT DOCUMENTS

| | | | |
|---|---|---|---|
| 4,161,943 A | 7/1979 | Nogier | |
| 4,346,715 A | 8/1982 | Gammell | |
| 4,442,404 A | 4/1984 | Bergmann | |
| 4,508,119 A | 4/1985 | Tukamoto | |
| 4,574,782 A | 3/1986 | Borrelli | |
| 4,590,922 A | 5/1986 | Gordon | |
| 4,675,286 A | 6/1987 | Calenoff | |
| 4,735,796 A | 4/1988 | Gordon | |
| 4,829,984 A | 5/1989 | Gordon | |
| 4,950,221 A | 8/1990 | Gordon | |
| 5,043,101 A | 8/1991 | Gordon | |
| 5,067,952 A | 11/1991 | Gudov | |
| 5,203,782 A | 4/1993 | Gudov | |
| 5,231,000 A | 7/1993 | Majocha | |
| 5,384,109 A | 1/1995 | Klaveness | |
| 5,486,161 A | 1/1996 | Lax | |
| 5,496,534 A | 3/1996 | Klaveness | |
| 5,506,500 A * | 4/1996 | Krause et al. | 324/201 |
| 5,715,837 A | 2/1998 | Chen | |
| 5,735,279 A | 4/1998 | Klaveness | |
| 5,738,837 A | 4/1998 | Klaveness | |
| 5,759,793 A | 6/1998 | Schwartz | |
| 5,782,764 A | 7/1998 | Werne | |
| 5,921,244 A | 7/1999 | Chen | |
| 5,935,123 A | 8/1999 | Edwards | |
| 6,203,487 B1 | 3/2001 | Consigny | |
| 6,348,185 B1 | 2/2002 | Piwnica-Worms | |
| 6,400,980 B1 | 6/2002 | Lemelson | |
| 6,459,924 B1 | 10/2002 | Creighton | |
| 6,470,220 B1 | 10/2002 | Kraus | |
| 6,485,985 B1 | 11/2002 | Weitschies | |
| 6,660,002 B1 | 12/2003 | Edwards | |
| 6,739,342 B1 | 5/2004 | Fredriksson | |
| 6,821,504 B2 | 11/2004 | Wisniewski | |
| 6,958,062 B1 | 10/2005 | Gough | |
| 6,960,196 B2 | 11/2005 | Prindle | |
| 6,997,863 B2 | 2/2006 | Handy | |
| 7,053,109 B2 | 5/2006 | Schostarez | |
| 7,074,175 B2 | 7/2006 | Handy | |
| 7,081,123 B2 | 7/2006 | Merboth | |
| 7,459,145 B2 | 12/2008 | Bao | |
| 7,662,362 B2 | 2/2010 | Kuppusamy | |
| 7,745,001 B2 | 6/2010 | Rosenzweig | |
| 7,906,345 B2 | 3/2011 | Wang | |
| 2002/0123079 A1 * | 9/2002 | Chen | 435/7.22 |
| 2002/0177769 A1 * | 11/2002 | Orbach et al. | 600/409 |
| 2003/0028071 A1 | 2/2003 | Handy | |
| 2003/0149354 A1 * | 8/2003 | Bakharev | 600/407 |
| 2004/0156784 A1 | 8/2004 | Haase | |
| 2004/0253181 A1 | 12/2004 | Port | |
| 2005/0090732 A1 | 4/2005 | Ivkov | |
| 2005/0249817 A1 | 11/2005 | Haik | |
| 2006/0093555 A1 | 5/2006 | Torres | |
| 2006/0140871 A1 | 6/2006 | Sillerud | |
| 2006/0142749 A1 | 6/2006 | Ivkov | |
| 2007/0037297 A1 | 2/2007 | Yoshinaga | |
| 2007/0112339 A9 | 5/2007 | Ivkov | |
| 2007/0140974 A1 | 6/2007 | Torres | |
| 2007/0148095 A1 | 6/2007 | Chen | |
| 2007/0166232 A1 | 7/2007 | Cho | |
| 2007/0197900 A1 | 8/2007 | Baudenbacher | |
| 2007/0205767 A1 * | 9/2007 | Xu et al. | 324/304 |
| 2007/0282200 A1 | 12/2007 | Johnson | |
| 2008/0093219 A1 | 4/2008 | Goldberg | |
| 2009/0074673 A1 | 3/2009 | Janjic | |
| 2009/0156659 A1 | 6/2009 | Butters | |
| 2009/0169478 A1 | 7/2009 | Leuschner | |
| 2009/0243610 A1 | 10/2009 | Ichihara | |
| 2009/0295390 A1 | 12/2009 | Hahn | |
| 2010/0008862 A1 | 1/2010 | Fu | |
| 2010/0021391 A1 | 1/2010 | Douglas | |
| 2010/0047180 A1 | 2/2010 | Zeng | |
| 2010/0120679 A1 | 5/2010 | Xu | |
| 2010/0188075 A1 | 7/2010 | Litvinov | |
| 2010/0219824 A1 | 9/2010 | Sillerud | |
| 2012/0035458 A1 | 2/2012 | Flynn | |
| 2012/0149029 A1 | 6/2012 | Flynn | |

FOREIGN PATENT DOCUMENTS

| | | |
|---|---|---|
| WO | WO2007/021621 | 2/2007 |
| WO | WO2008/133726 | 11/2008 |
| WO | PCT/US2010/051417 | 5/2011 |
| WO | PCT/US2010/055729 | 5/2011 |
| WO | PCT/US2011/28746 | 9/2011 |
| WO | PCT/US2011/036349 | 12/2011 |

OTHER PUBLICATIONS

Jaetao et al., Enhanced Leukemia Cell Detection Using a Novel Magnetic Needle and Nanoparticles, Nov. 1, 2009, Cancer Research, Bol. 69, ls. 21, p. 8310-8316.

Stéphane Mornet Sébastien Vasseur, Fabien Grasset and Etienne Duguet, "Magnetic nanoparticle design for medical diagnosis and therapy" Journal of Materials Chemistry, 2004, 14, 2161-2175. retrieved from URL: http://pubs.rsc.org/en/content/articlelanding/2004/jm/b402025a.

Y. R. Chemla H. L. Grossman, Y. Poon, McDermott, R. Stevens, M. D. Alper, and J. Clarke, "Ultrasensitive magnetic biosensor for homogeneous immunoassay" Proc Natl Acad Sci U S A. Dec. 19, 2000; 97(26): 14268-14272, retrieved from URL: http://www.ncbi.nlm.nih.gov/pmc/articles/PMC18907/.

Leslie Laconte Nitin Nitin, Gang Bao, "Magnetic nanoparticle probes", Materials Today, vol. 8, Issue 5, Supplement 1, May 2005, pp. 32-38, ISSN 1369-7021, retrieved from URL: http://www.sciencedirect.com/science/article/B6X1J-4G2FPKY-W/2/1301571fec686ec339a119ab10a5e17d.

Nanotechnology tackles brain cancer, National Cancer Institute Alliance for Nanotechnology in Cancer, Dec. 2005, 1-4.

Cecchelli, Romeo et al. Modelling of the blood-brain barrier in drug discovery and development, Nature Publishing Group, vol. 6 Aug. 1007, 650-661.

Cengelli, Feride et al. Interaction of functionalized superparamagnetic iron oxide nanoparticles with brain structures. The Journal of Pharmacology and Experimental Therapeutics vol. 318, No. 1 2006, 108-116.

Flynn, E.R. et al. A biomagnetic system for in vivo cancer imaging. Institute of Physics Publishing, Physics in Medicine and Biology. Phys. Med. Bio. 50 2005, 1273-1293.

Flynn, E.R. et al. Use of a SQUID array to detect T-cells with magnetic nanoparticles in determing transplant rejection. Journal of Magnetism and Magnetic Materials. Www.sciencedirect.com Dec. 2006, 429-435.

Haller, Andreas et al. Low TcSQUID measurement system for magnetic relaxation immunoassays in unshielded environment. IEEE Transactions on Applied Superconductivity, vol. 11, No. 1, Mar. 2001, 1371-1374.

Huddleston, Dan E. et al. Technology Insight: imaging amyloid plaques in the living brain with positron emission tomography and MRI. Nature Publishing Group vol. 1 No. 2. Dec. 2005, 96-105.

Michaelis, K. et al. Covalent linkages of apoliprotein E to albumin nanoparticles strongly enhances drug transport into the brain. The Journal of Pharmacology and Experimental Therapeutics. vol. 317, No. 3 2006. 1246-1253.

Reddy, G.R. et al. Vascular targeted nanoparticles for imaging and treatment of brain tumors. American Association of Cancer Research. Www.aacrjournals.org. Nov. 15, 2006, 6677-6686.

Small, Gary W. et al. PET of brain amyloid and tau in mild cognitive impairment. The New England Journal of Medicine. Dec. 2006, 2652-2663.

* cited by examiner

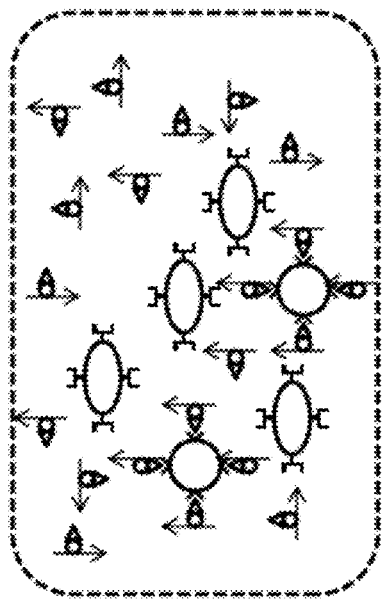
Fig. 2a
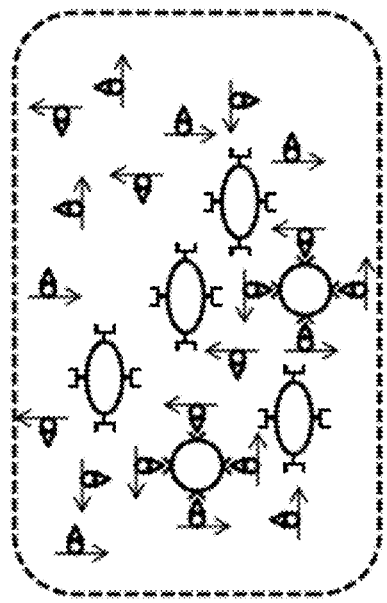
Fig. 2b
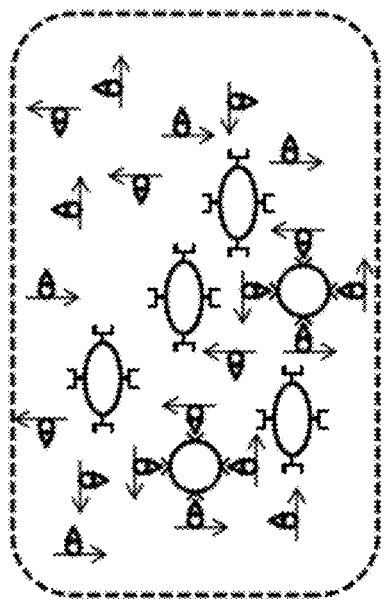
Fig. 2a
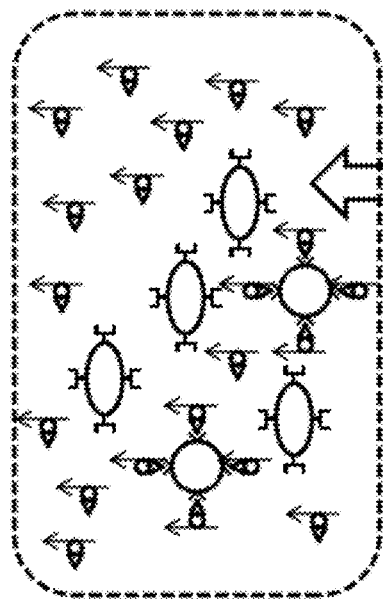
Fig. 2b
Fig. 2

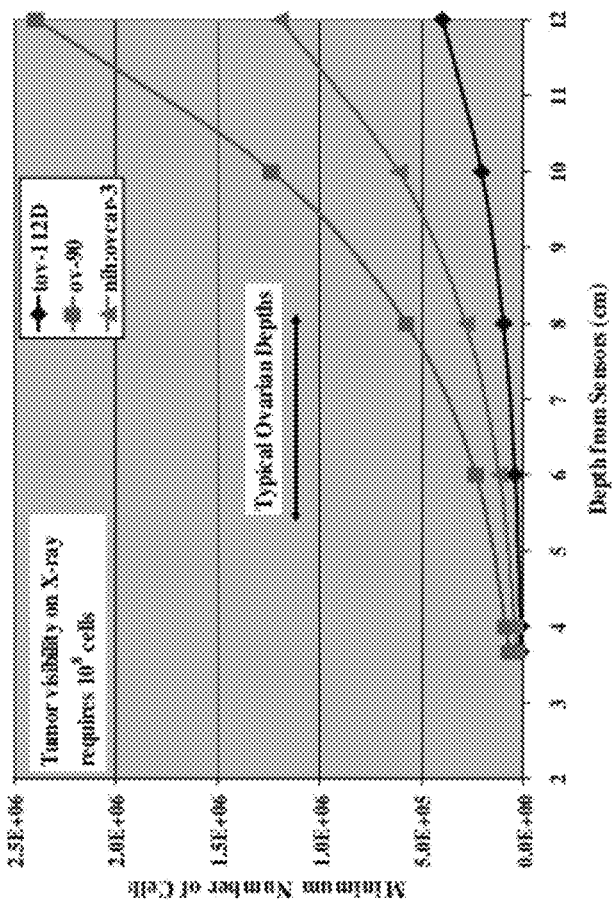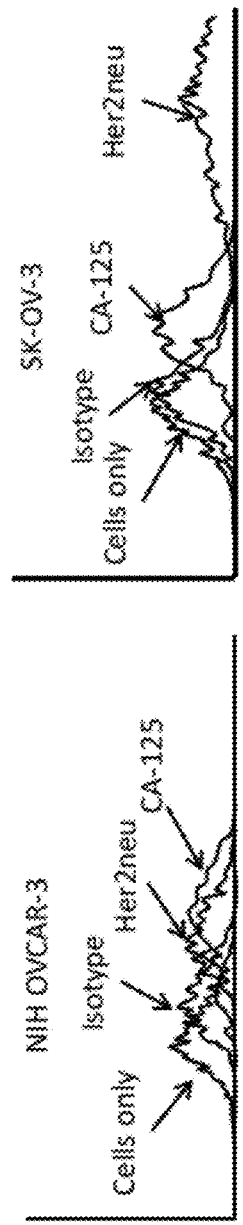
Fig. 22
Fig. 23a
Fig. 23b

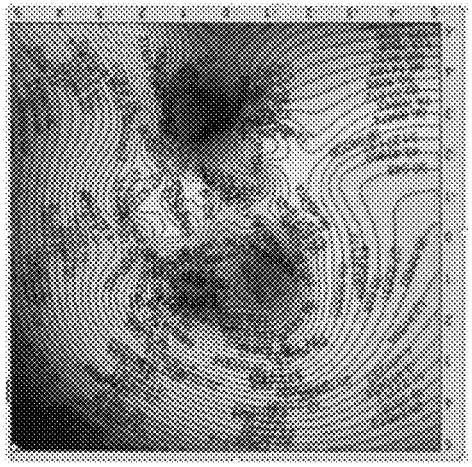
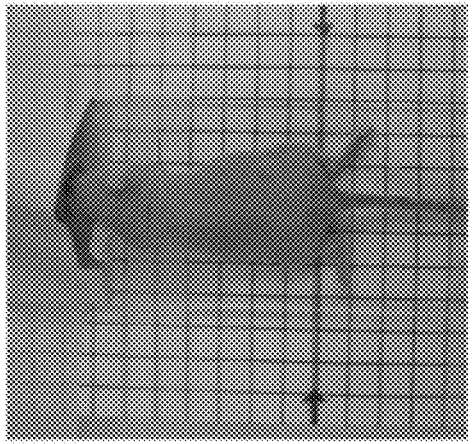
Fig. 25
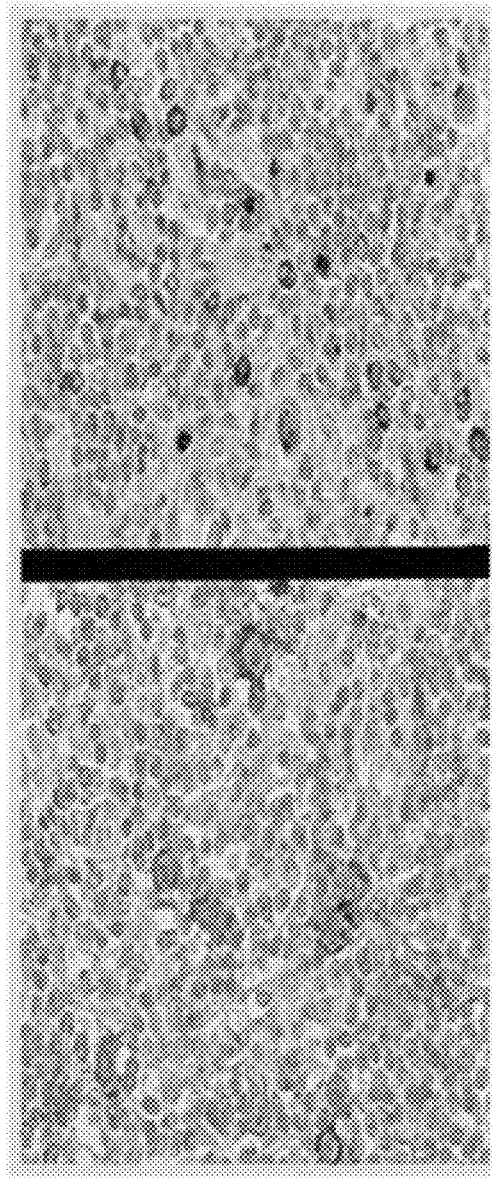
Fig. 28

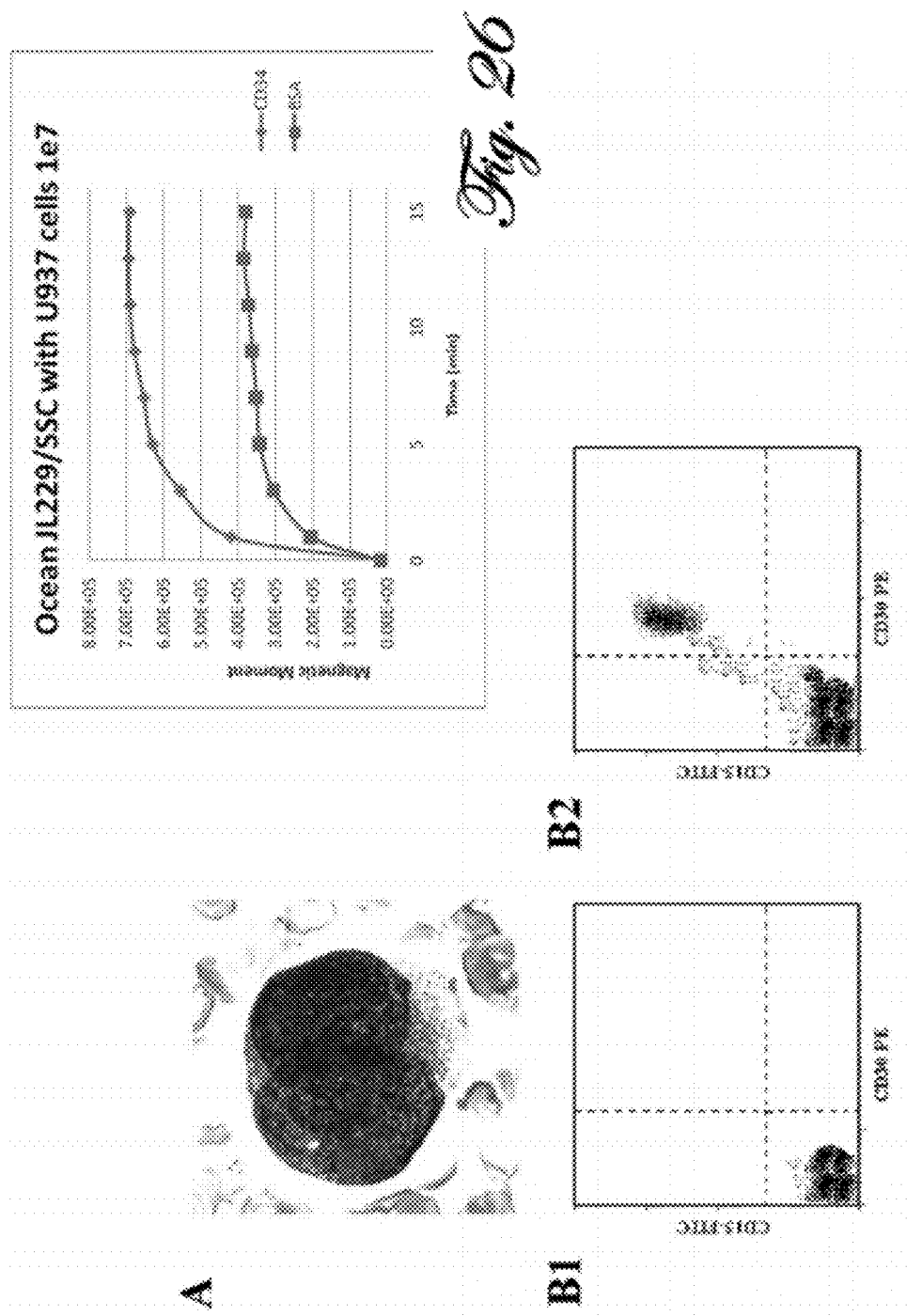

DETECTION, MEASUREMENT, AND IMAGING OF CELLS SUCH AS CANCER AND OTHER BIOLOGIC SUBSTANCES USING TARGETED NANOPARTICLES AND MAGNETIC PROPERTIES THEREOF

CROSS REFERENCE TO RELATED APPLICATIONS

This invention claims priority to U.S. application 61/386,961 filed Sep. 27, 2010; and to U.S. application 61/389,233 filed Oct. 3, 2010;
and as a continuation in part of U.S. application Ser. No. 11/940,673 filed Nov. 15, 2007, now U.S. Pat. No. 8,060,179 which application claimed priority to U.S. application 60/866,095 filed Nov. 16, 2006;
and as a continuation in part of U.S. application Ser. No. 12/337,554 filed Dec. 17, 2008, now U.S. Pat. No. 8,118,754 which application was a continuation in part of U.S. application Ser. No. 11/957,988 filed Dec. 17, 2007, now abandoned which application was a continuation in part of U.S. application Ser. No. 11/940,673 filed Nov. 15, 2007; now U.S. Pat. No. 8,060,179
and as a continuation in part of PCT application PCT/US2010/051417 filed Oct. 5, 2010, which application claimed priority to U.S. application 61/248,775 filed Oct. 5, 2009, U.S. application 61/329,076 filed Apr. 28, 2010, and U.S. application 61/377,854 filed Aug. 27, 2010;
and as a continuation in part of PCT application PCT/US2010/055729 filed Nov. 5, 2010, which application claimed priority to U.S. application 61/314,392 filed Mar. 16, 2010, U.S. application 61/331,816 filed May 5, 2010, U.S. application 61/361,998 filed Jul. 7, 2010, U.S. application 61/259,011 filed Nov. 6, 2009, U.S. application 61/308,897 filed Feb. 27, 2010, and U.S. application 61/310,700 filed Mar. 4, 2010;
and as a continuation in part of PCT application PCT/US2011/28746 filed Mar. 16, 2011, which application claimed priority to U.S. application 61/314,370 filed Mar. 16, 2010; and claims priority to U.S. application 61/454,560 filed Mar. 20, 2011.

Each of the preceding applications and patents is incorporated herein by reference.

FIELD OF THE INVENTION

This invention relates to the in vivo detection and measurement of cells or substances using targeted nanoparticles and magnetic relaxation measurements, and is particularly useful in detecting and measuring cancer cells in humans.

BACKGROUND OF THE INVENTION

Early detection and accurate measurement of disease allows the maximum likelihood of successful treatment and recovery. Furthermore, early detection and localization of the disease can permit directed therapy to the site of the disease optimizing the efficiency of the treatment. With an appropriate detection device, the treatment can be monitored, further increasing the efficacy of the applied drugs or other forms of therapy. The ability to target specific diseases can also improve treatment outcomes. Early detection and localization of cancer, the second leading cause of death in the US, can improve patient outcomes. Early detection, as used herein, refers to the initial detection of the presence of cancer as well as the detection of metastases, in each case while the tumor or metastases are relatively small or early in their growth process. Early detection also refers to detection of small changes in the size or other characteristics of tumors. Much of the discussion herein refers to in vivo cancer for ease of illustration; the invention is applicable to other biological conditions such as measurement of Amyloid plaque (e.g., by targeting plaque) and characterization of immune system response such as in monitoring transplant status or immunotherapy (e.g., by targeting T cells), as well as ex vivo operation such as in evaluating cell cultures, biopsies, or other tissue samples.

Many common methods used for clinical purposes for detection of cancer are non-specific, i.e., they cannot distinguish between cancerous or benign tumors and none lead to 100% accurate detection. The available methods all have disadvantages and weaknesses, resulting in high rates of false diagnosis and too low a rate of positive diagnosis, together leading to increased mortality rates. The most common clinical modalities presently available are: (1) X-ray mammography, (2) magnetic resonance imaging (MRI), and (3) ultrasound scanning with (4) positron-emission tomography (PET) an additional option when available.

The measurement of X-ray attenuation provides information on the density of the intervening medium. X-rays are FDA approved and are the most common technique used to detect various forms of disease and, in particular, cancer. It is also responsible for many false-negative and false-positive results. Early stage cancer tumors can be detected but without specificity with regard to benign or cancerous tumors. Artifacts can be caused by healthy tissue and give rise to false positive results. Irregularities in tissue such as scarring can cause non-uniform scattering of the x-rays rendering mammograms ineffective. Although the dose is low, there is increasing concern about the exposure to X-rays and radiation in general. Overall, the number of false positives in x-ray imaging of cancer remains high and the x-ray method cannot detect early-stage tumors.

Ultrasound is used to provide a method for imaging tumors. Ultrasound has excellent contrast resolution but suffers from diminished spatial resolution compared to x-rays and other imaging techniques. Ultrasound is non-specific to cancer versus benign tissue. Ultrasound is not currently approved by the FDA as a primary screening tool for cancer but is normally used as a follow up to investigate any abnormalities detected during routine examinations. It is often used to confirm suspect areas in x-ray images of breast and ovarian cancer.

MRI is used to follow up on potential problem areas seen during x-ray scans; however, the expense of a MRI scan often prohibits its use. MRI can detect small abnormalities in tissue and also can be useful in determining if cancer has metastasized. Dynamic Contrast Enhanced (DCE) MRI potentially distinguishes between benign and cancerous tumors but produces a number of false positives. The expense of MRI limits its application as a screening tool. MRI imaging of cancer can use magnetic nanoparticles as contrast agents and is an accepted protocol providing standards for the injection of such nanoparticles. Intravascular MRI contrast agents at a dose of 2 mg/kg of nanoparticle weight have been proposed to detect metastatic lesions. MRI detection of contrast is subjective and relies on the expertise of the physician reading the scans.

Because of the importance of early detection of disease, there are a variety of other techniques currently being studied for imaging. These include scintimammography using PET or SPECT, Impedance Tomography, and various forms of RF imaging.

Early detection of lesions while they are still contained is crucial, since the cure rate of many cancers detected early is near 100%. Existing imaging methods often do not identify lesions until significant growth has occurred. There is ongoing research in alternative methods, including MRI, PET, ultrasound, scintigraphy, and other methods. At present, none of these methods have specificity regarding tumor type using differences in tissue properties between cancerous and non-cancerous tissue. In particular, a new approach not relying on harmful radiation, or very expensive procedures, and offering very early detection of tumors is clearly needed. The present invention provides new capabilities for in-vivo detection and measurement of cancer and other targetable biological substances.

SUMMARY OF THE INVENTION

The present invention can provide a method of determining the presence, location, quantity, or a combination thereof, of a biological substance, comprising: (a) exposing a sample to a plurality of targeted nanoparticles, where each targeted nanoparticle comprises a paramagnetic nanoparticle conjugated with one or more targeting agents that preferentially bind with the biological substance, under conditions that facilitate binding of the targeting agent to at least one of the one or more biological substances, under conditions that facilitate binding of the targeting agent to one or more of the biological substances; (b) subjecting the sample to a magnetic field of sufficient strength to induce magnetization of the nanoparticles; (c) measuring a magnetic field of the sample after decreasing the magnetic field applied in step b below a threshold; (d) determining the presence, location, quantity, or a combination thereof, of the one or more biologic substances from the magnetic field measured in step c. In the plurality of targeted nanoparticles, each nanoparticle can be conjugated with the same targeting agent (to measure only substances targeted by that targeting agent), the targeted nanoparticles can be conjugated with more than one different targeting agents (multiple targeting agents per nanoparticle, or some nanoparticles conjugated with one targeting agent while other nanoparticles conjugated with other targeting agents) (to measure any of the substances targeted by any of the targeting agents).

Determining the "presence, location, quantity, or a combination thereof" includes without limitation determining whether a substance is present, the quantity of a substance present, the concentration of a substance present, the location of a substance within a region of interest, and combinations thereof and alternatives thereto. A "biological substance" includes without limitation cells, cells of particular types or having particular characteristics, proteins, plaques such as Amyloid plaque, and other substances such as epithelial growth factor. A "sample" includes without limitation a portion of tissue or other material removed from a body, a portion of a human body such as an organ or region including an organ, an entire body, and a cell culture. "Paramagnetic nanoparticles" include paramagnetic and superparamagnetic nanoparticles, including as examples those described in U.S. application 61/329,076 filed Apr. 28, 2010, which application is incorporated herein by reference. "Conjugated with a targeting agent" includes without limitation all techniques by which nanoparticles can be placed in a relatively fixed relationship with a targeting agent, as examples including those techniques described in any of the applications incorporated herein by reference. A "targeting agent" includes any agent that can be used to bind with a substance of interest in preference to another portion of a sample, and includes without limitation antibodies and peptides.

In some example embodiments, the nanoparticles comprise superparamagnetic nanoparticles. In some example embodiments, the nanoparticles comprise iron oxide particles having a diameter of about 24 nm, or iron platinum particles having a diameter of about 15 nm. In some example embodiments, the magnetic field in step b has a strength of at least 50% of that required to completely saturate the magnetization of the nanoparticles. In some example embodiments, the magnetic field in step b is applied with sufficient strength and for sufficient time to align the magnetic moments of at least 20% of the nanoparticles. In some example embodiments, the magnetic field in step b is applied with sufficient strength and for sufficient time to align the magnetic moments of at least 50% of the nanoparticles. In some example embodiments, the magnetic field in step b is applied with sufficient strength and for sufficient time to align the magnetic moments of at least 80% of the nanoparticles. In some example embodiments, the magnetic field in step b is applied with sufficient strength and for sufficient time to align the magnetic moments of more than 95% of the nanoparticles.

In some example embodiments, step d comprises determining a spatial distribution of the nanoparticles. In some example embodiments, step d comprises solving an inverse electromagnetic problem to determine locations of magnetic sources in the sample.

Some example embodiments further comprise repeating steps b through d a plurality of times and averaging the magnetic field measurement in step c, the particle determination in step d, or a combination thereof, of two or more of such repetitions of steps c through d. In some example embodiments, measuring the magnetic field in step c comprises measuring the magnetic field over a period of time. In some example embodiments, step d comprises fitting a decay curve of the magnetic field as measured over a period of time to a log/exponential function to determine the magnetic field of the sample at the time the magnetic field was decreased in step b.

The present invention can also provide an apparatus for the determination of the presence, location, quantity, or a combination thereof, of a biological substance, comprising: (a) a magnetization system, configured to subject a sample to a magnetic field, wherein the sample has been exposed to a plurality of targeted nanoparticles, where each targeted nanoparticle comprises a paramagnetic nanoparticle conjugated with one or more targeting agents that preferentially bind with the biological substance, under conditions that facilitate binding of the targeting agent to at least one of the one or more biological substances, under conditions that facilitate binding of the targeting agent to one or more of the biological substances; wherein the magnetic field has sufficient strength to induce magnetization of the nanoparticles; (b) a magnetic measurement system, configured to measure a magnetic field of the sample after a magnetic field applied by the magnetization system has been decreased below a threshold; (c) an analysis system, configured to determine the presence, location, quantity, or a combination thereof, of the one or more biologic substances from the magnetic field measured by the magnetic measurement system.

In some example embodiments, the magnetization system comprises one or more Helmholtz coils. In some example embodiments, the magnetic measurement system comprises one or more superconducting quantum interference devices. In some example embodiments, the magnetic measurement system comprises one or more atomic magnetometers. In some example embodiments, the magnetic measurement system comprises one or more magnetic sensors coupled to one or more second order gradiometers. In some example embodiments, the magnetic measurement system comprises a plurality of magnetic sensors configured to measure spatial characteristics of the magnetic field, and wherein the analysis system is configured to determine spatial distribution of the nanoparticles from the spatial characteristics of the magnetic field. In some example embodiments, the magnetic measurement system is configured to measure the decay of the magnetic field over a period of time.

The present invention can provide apparatuses and methods to detect cells or substances, for example cancer cells, Amyloid plaque, and T-cells, in tissue samples. Some example embodiments comprise a magnetic system, including a magnetic field generator that imposes a known magnetic field on a sample, such as the tissue of the subject, magnetizing targeted paramagnetic nanoparticles bound to the cells or substance of interest; and a sensitive magnetic sensor that can detect the residual magnetic field as the magnetization of the nanoparticles decays. An example magnetic system comprises a superconducting quantum interference device sensor comprising a magnetic pulse circuit, adapted to apply a uniform magnetizing pulse field to a cancer tissue of a patient placed on a measurement stage; and a remnant magnetic field detector, adapted to detect and image the residual magnetic field produced by the applied pulsed field. The magnetic pulse circuit can comprise a pair of Helmholtz coils. The remnant magnetic field detector can comprise an array of gradiometers.

Another example magnetic system comprises an atomic magnetometer and an array of atomic gradiometers—very sensitive magnetic field sensors that can be used to measure extremely weak magnetic fields based on the Larmor precession of atoms in a magnetic field. In some embodiments of the present invention, the atomic magnetometer comprises a chip set containing a small cavity containing an atomic vapor cell. This vapor cell contains Rb atoms, and is optically pumped by circularly polarized laser beam. The atoms go through a Larmor precession and the frequency of this precession causes a change in the index of refraction of the vapor in response to an applied magnetic field. A second laser can be used as a measuring field for this change in refraction using a set of gratings to measure interference pattern changes as the applied magnetic field changes. The vapor cells can be single or arranged in a gradiometer configuration to measure the changes in field as a function of distance.

An example method according to the present invention comprises providing the magnetic system; injecting a plurality of targeted (e.g., labeled with an antibody) paramagnetic nanoparticles into a subject for specific binding to the cancer cells or other cells or substance of interest; applying a known (e.g., uniform) magnetizing pulse field to magnetize the nanoparticles in the subject tissue; and detecting the residual magnetic field of the magnetized nanoparticles thereby providing an image of the nanoparticles bound to the cancer tissue of the patient. The targeted paramagnetic nanoparticle can comprise a magnetic core coated with a biocompatible coating to which is attached at least one specific antibody. For example, the magnetic core can comprise a ferromagnetic material, such as iron oxide. Examples of suitable targeting agents such as antibodies are described below.

In some embodiments of the present invention, the size and extent of a tumor can be determined by computer-aided analysis using techniques such as minimum norm and multipole expansions. In some embodiments of the present invention, the location of the bound nanoparticles can be presented in combination with image information such as can be obtained from Xray instruments, photographs, or MRIs. In some embodiments of the present invention, measurements on phantoms can be used in combination with electromagnetic theory to determine location accuracy and detection sensitivity at various depths. In some embodiments of the present invention, the magnetic moment measured can be used to determine a number of nanoparticles bound to targeted cells, or a number of targeted cells having bound nanoparticles, using the characteristic that the magnetic moment is linearly related to the number of bound nanoparticles.

The present invention is described in terms of various example applications, including applications to the measurement of specific types of cancer cells. The invention is not limited to such examples, however. The invention can be useful in determining properties such as the presence of a biological substance in a sample, the location of a quantity of a biological substance in a sample, the quantity of a biological substance in a sample (e.g., the number of cancer cells in a tumor), or a combination thereof.

BRIEF DESCRIPTION OF DRAWINGS

The accompanying drawings, which are incorporated in and form part of the specification, illustrate the present invention and, together with the description, describe the invention. In the drawings, like elements are referred to by like numbers.

FIG. 2($a,b,c,d$) provide a schematic illustration of an example measurement in accord with the present invention.

FIG. 22 is an illustration of the results of sensitivity studies for live ovarian cells inserted into the phantom shown in FIG. 21.

FIG. 23 is an illustration of confirmation of antibody sites for these cells using flow cytometry.

FIG. 25 is a photograph of a mouse used to verify that the SQUID sensor method works in-vivo along with magnetic contour fields from the mouse.

FIG. 26 is a graph of a measurement of the magnetic moment in a SQUID sensor system as a function of time for incubation of attaching magnetic nanoparticles to lymphoma cell lines.

FIG. 27 is an illustration of the results of the flow cytometric measurements of RS cells from the lymphatic system in determining the number of sites available for nanoparticles and detection by the SQUID sensors.

FIG. 28 is a histology slice from a patient with Hodgkin's Disease.

DETAILED DESCRIPTION OF THE INVENTION

The present invention is described in the context of various example embodiments and applications. In some of the description, the term "detection" is used for brevity; the invention can provide for the detection of the presence of cells or substances, measurement of the number of cells or amount of substance, determination of the location of cells or substance, determination of the change or rate of change in the preceding, and similar determinations, all of which are included in the term "detecting."

Figure 1:
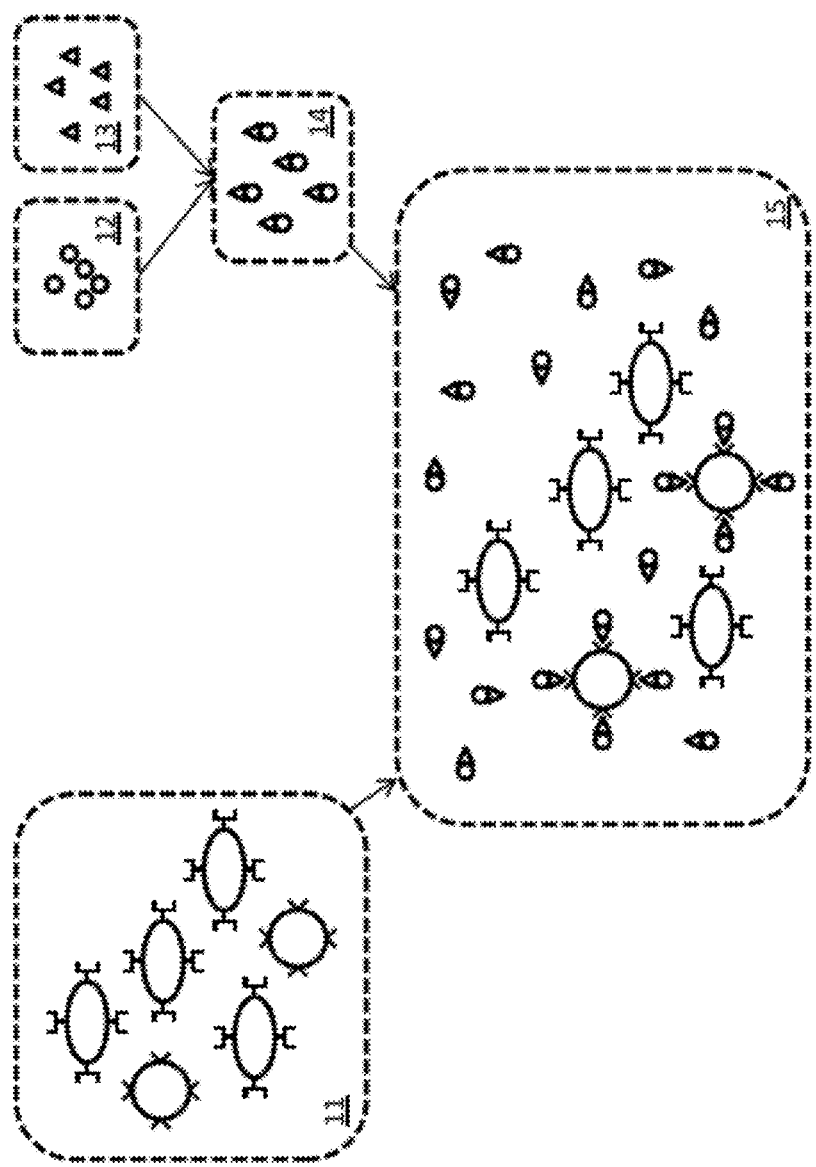
FIG. 1 is a schematic illustration of an example preparation of tissue of a subject for measurement according to the present invention.

A simplified example of magnetic relaxation measurement according to the present invention is first described. FIG. 1 is a schematic illustration of an example preparation of a sample for measurement according to the present invention. The illustrations in the figure are highly simplified and intended for ease of explanation only, and are not intended to represent the actual shapes, sizes, proportions, or complexities of the actual materials involved. A portion of the tissue 11, e.g., an organ to be investigated, or a known or suspected tumor site, or a cell culture, or a sample removed from a body, comprises some cells of the type of interest (shown in the figure as circles with "V" shaped structures around the periphery) and some cells of other types (shown in the figure as ovals with rectangular structures around the periphery). A plurality of magnetic nanoparticles 12 is provided, shown in the figure as small circles. A plurality of targeting molecules 13 is also provided, shown in the figure as small triangles. The nanoparticles and targeting molecules are combined (or conjugated), forming targeted nanoparticles 14.

The targeted nanoparticles can then be introduced to tissue 15. Cells of the type of interest have binding sites or other affinities for the targeting molecule, illustrated in the figure by "V" shaped structures around the periphery of such cells. The targeting molecules attach to the cells of the type of interest, illustrated in the figure by the triangular targeting molecules situated within the "V" shaped structures. Generally, each cell will have a large number of such binding or affinity sites. Cells of other types do not have such binding sites or affinities, illustrated in the figure by ovals with no targeted nanoparticles attached. Targeted nanoparticles that do not bind to cells are left free in the prepared sample, illustrated in the figure by small circles with attached triangles that are not connected with any specific cell.

FIG. 2($a,b,c,d$) provide a schematic illustration of an example measurement in accord with the present invention. In FIG. 2$a$, the sample is as in FIG. 1, with the addition of arrows near each nanoparticle. The arrows are representative of the magnetization of each nanoparticle, and indicate that the magnetization of the nanoparticles in the tissue is random (in the figure, the arrows are shown in one of four directions for ease of illustration only; in practice the magnetization can have any direction).

In FIG. 2$b$, an external magnetic field (represented by the outlined arrow at the lower right of the figure) is applied. The magnetization of the nanoparticles in response to the applied magnetic field is now uniform, represented in the figure by all the magnetization arrows pointing in the same direction.

FIG. 2$c$ illustrates the tissue a short time after the magnetic field is removed. The nanoparticles not bound to cells are free to move by Brownian motion, and their magnetization rapidly returns to random, represented in the figure by the magnetization arrows of the unbound nanoparticles pointing in various directions. The nanoparticles bound to cells, however, are inhibited from such physical motion and hence their magnetization remains substantially the same as when in the presence of the applied magnetic field.

FIG. 2$d$ illustrates the prepared sample a longer time after removal of the applied magnetic field. The magnetization of the bound nanoparticles has by now also returned to random.

Figure 3:
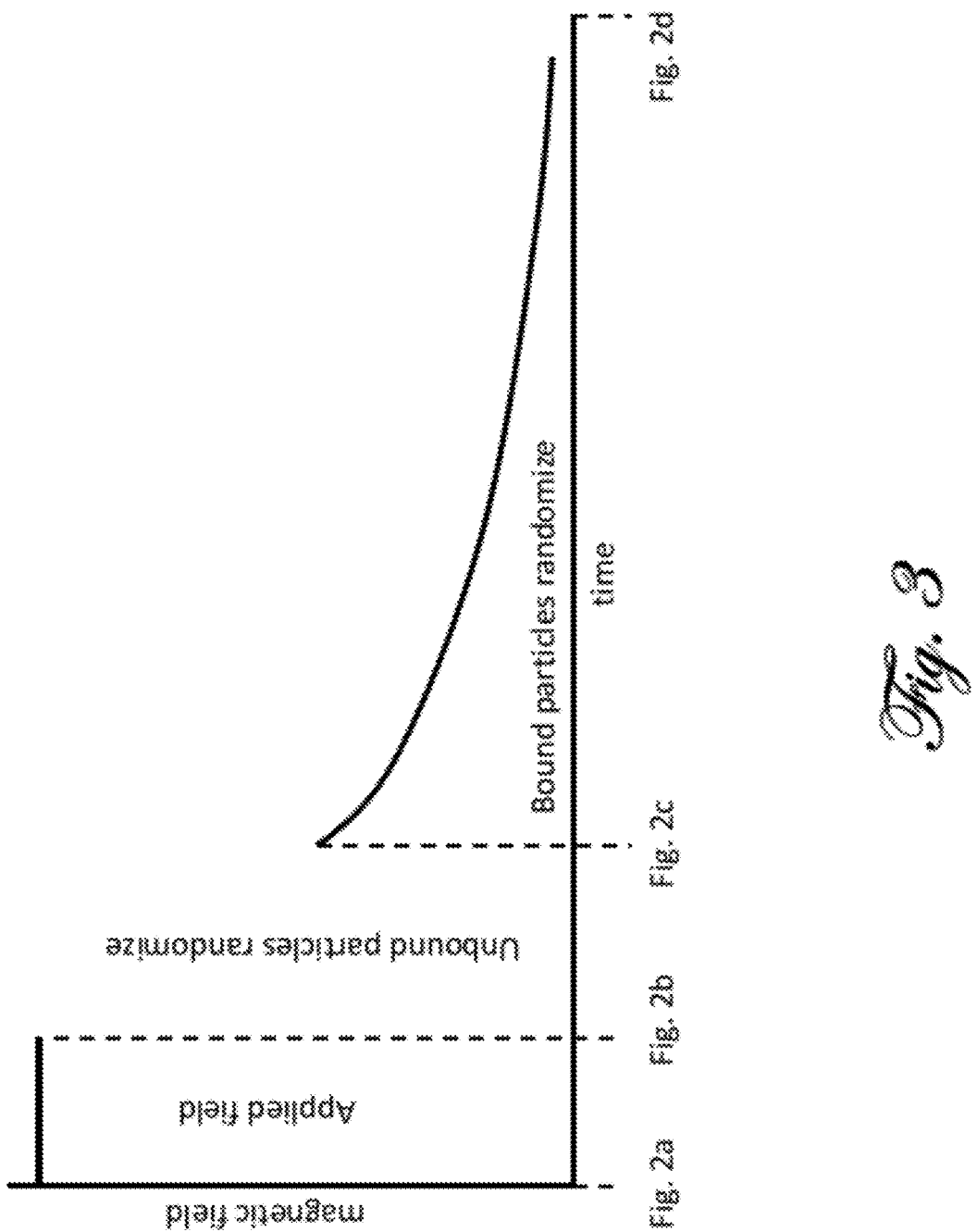
FIG. 3 is a schematic illustration of measurements from the process described in connection with FIG. 2.

FIG. 3 is a schematic illustration of measurements from the process described in connection with FIG. 2. Magnetic field is shown as a function of time in a simplified presentation for ease of illustration; in actual practice the units, scales, and shapes of the signals can be different and more complex. At the beginning of the process, corresponding to the state of FIG. 2$a$, the nanoparticle magnetization is random and the external magnetic field is applied. After that time, the magnetization of the nanoparticles is uniform, corresponding to the state of FIG. 2$b$. The magnetic field can be ignored for a short time while the unbound nanoparticles return to random magnetization, corresponding to the state of FIG. 2$c$. The magnetization can then be measured as the bound nanoparticles transition from uniform to random magnetization, corresponding to the state of FIG. 2$d$. The characteristics of the measurement magnetization from the state of FIG. 2$c$ to that of FIG. 2$d$ are related to the number of bound nanoparticles in the sample, and hence to the number of cells of the type of interest in the sample.

Figure 4:
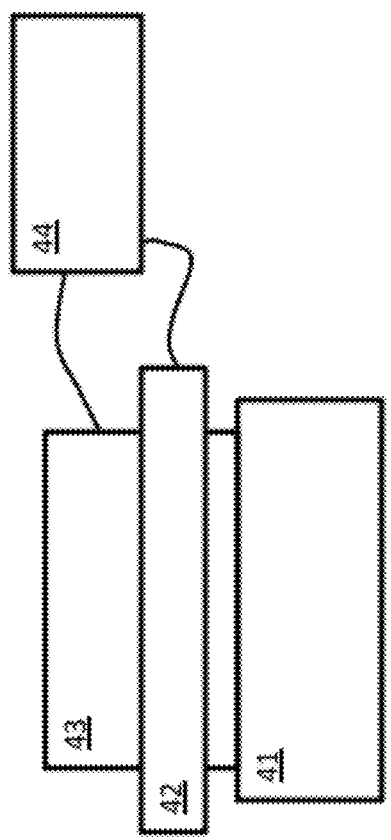
FIG. 4 is a schematic illustration of an apparatus suitable for use in the present invention.

FIG. 4 is a schematic illustration of an apparatus suitable for use in the present invention. A sample stage 41 is configured to dispose the sample in an effective relationship to the rest of the apparatus. A magnetizing system 42, for example Helmholtz coils, mounts relative to the sample stage so that the magnetizing system can apply a magnetic field to the sample. A magnetic sensor system 43 mounts relative to the subject sample so that it can sense the small magnetic fields associated with the magnetized nanoparticles. The system is controlled and the sensor data analyzed by a control and analysis system 44; for example by a computer with appropriate programming.

Figure 5:
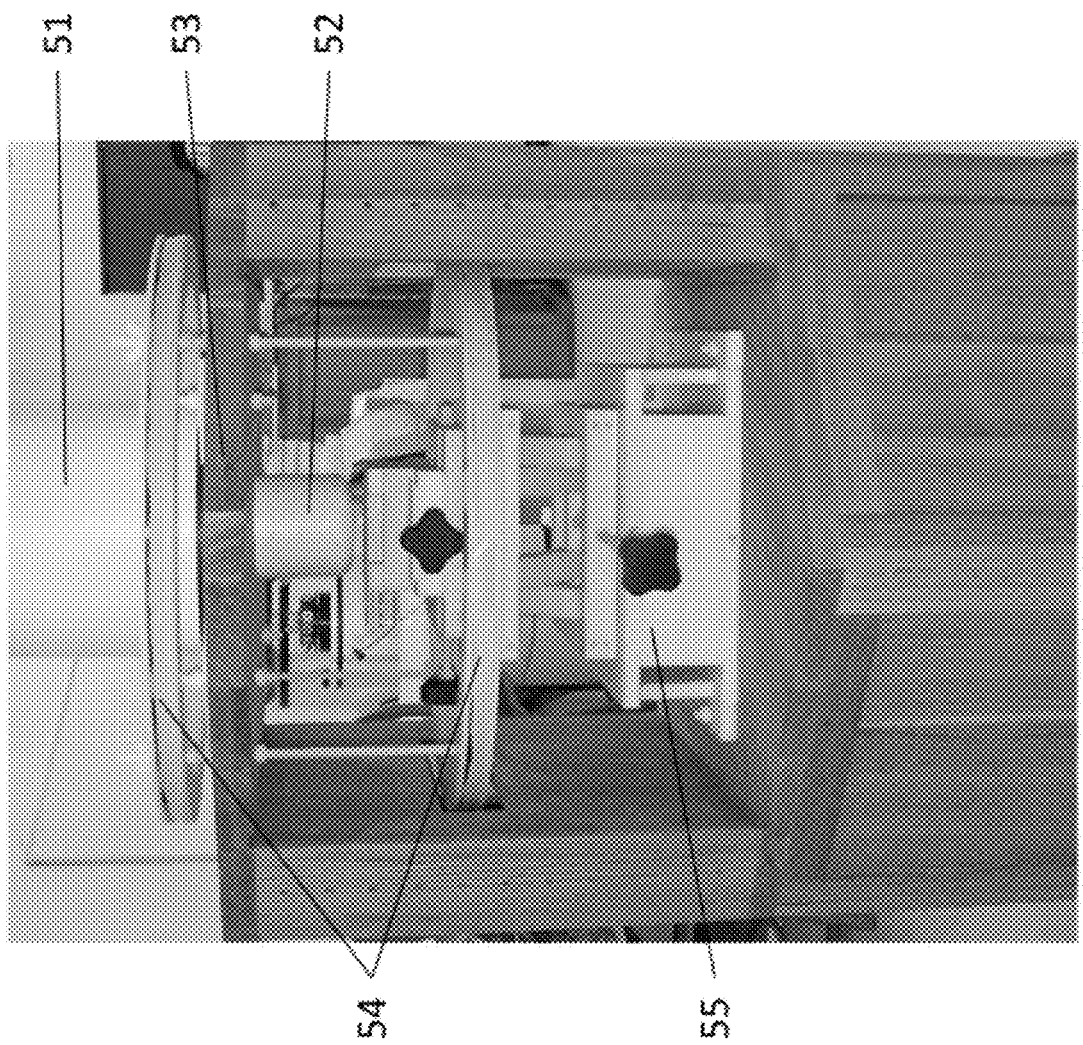
FIG. 5 is a schematic illustration of an exemplary apparatus using superconducting quantum interference device (SQUID) magnetic sensors.

FIG. 5 is a schematic illustration of an exemplary apparatus using superconducting quantum interference device (SQUID) magnetic sensors. A liquid helium reservoir dewar 51 at the top of the picture maintains the temperature of the SQUID sensors. SQUID 2nd-order axial gradiometers are contained in a white snout 52 protruding through a support frame 53. There are seven gradiometers with a baseline of 4 cm contained within this exemplary snout; one in the center and 6 in a circle of 2.0 cm radius. Each gradiometer is inductively coupled to a low temperature SQUID. Two circular coils 54 form a Helmholtz pair that can provide a magnetizing pulsed field for the nanoparticles. The uniform field produced by these coils can be varied but typically is 40 to 50 Gauss and the pulse length is typically 300-800 msec. In this example, a wooden frame supports the SQUID and the measurement platform as well as the magnetizing coils. The non-magnetic support system comprises a 3-dimensional stage 55 that can be constructed with no metal components, e.g., of plastic. The upper two black knobs control the x-y stage movements over a +/−10 cm range and the lower knob is used to raise and lower the measurement stage over a 20 cm range. A sample holder can be inserted onto the stage that can contain cultures of live cancer cells, phantoms containing vials of live cancer cells and live subjects such as mice or other small animals.

Figure 6:
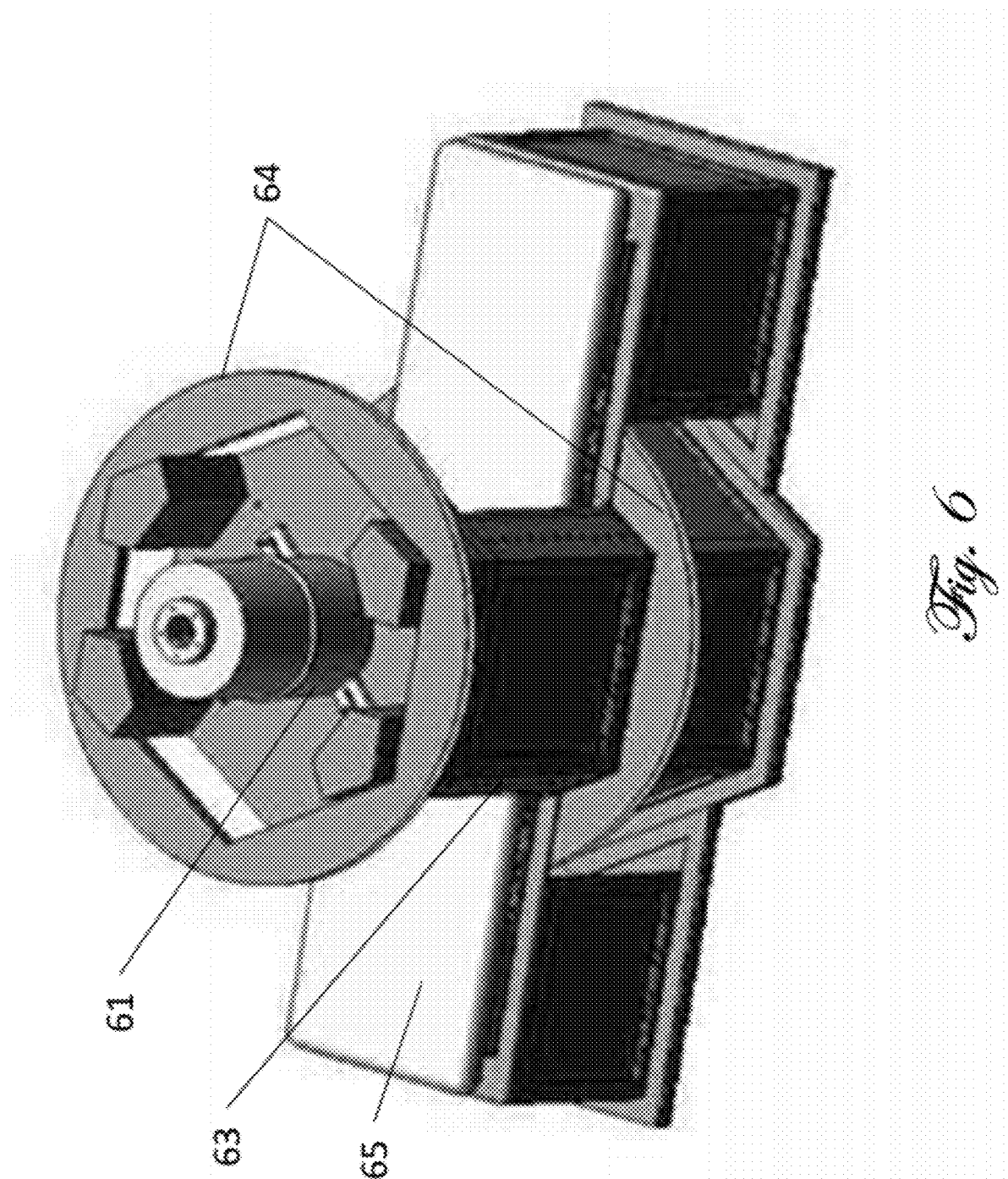
FIG. 6 is a schematic illustration of an exemplary SQUID sensor apparatus that can be used for human cancer examinations.

FIG. 6 is a schematic illustration of an exemplary SQUID sensor apparatus that can be used for human cancer examinations. A wooden structure 63 can be similar to the support frame shown in FIG. 5. The measurement stage can be replaced by a bed 65 for patient placement. Two larger Helmholtz coils 64 comprise the wooden circular forms above and below the bed. These larger coils can be used to generate a uniform pulse field and magnetize the magnetic nanoparticles that have been injected into the patient. The currents can be modified, e.g., increased, from those used in the apparatus shown in FIG. 5 to again produce fields in the range of 40 to 50 Gauss. Similar to the apparatus shown in FIG. 5, a SQUID dewar 61 with an array of magnetic gradiometers can be used to measure the residual magnetic field change produced by the magnetized nanoparticles.

Figure 7:
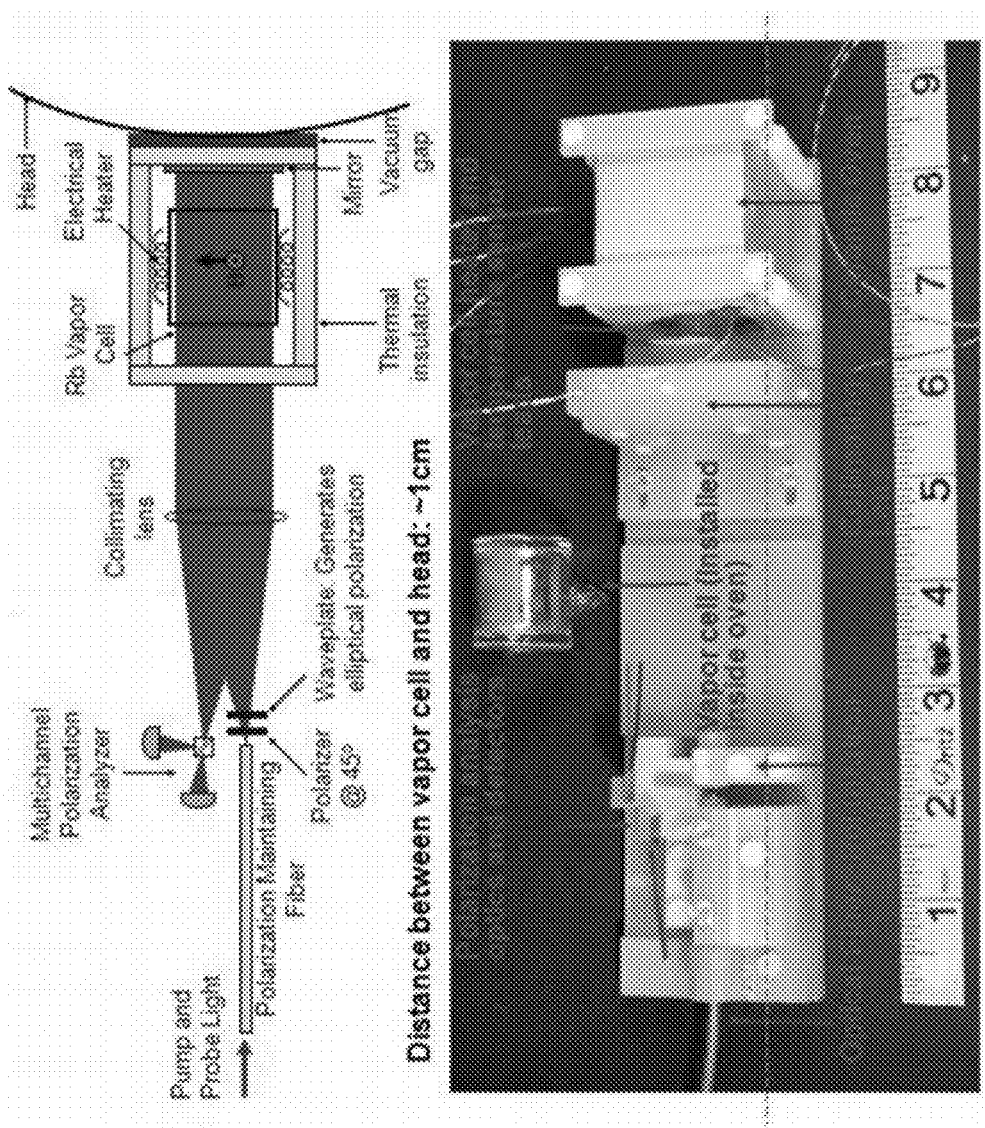
FIG. 7 is a schematic illustration and photo of an atomic magnetometer for weak field measurements.

FIG. 7 is a schematic and photo of an atomic magnetometer suitable for use with some embodiments of the present invention. This device is miniaturized by using microchip fabrication methods and multiple units can be placed side-by-side to form an array of sensors. The operation of the magnetometer is through application of a laser light beam applied through an optical fiber. This beam pumps the heated Rb gas in the vapor cell into specific atomic states. The beam is first elliptically polarized and collimated into the vapor cell. A mirror reflects this beam back through the cell and lens into a polarization analyzer. A magnetic field applied perpendicular to the length of the magnetometer changes the index of refraction of the gas in the cell, changing the polarization of the light through the cell. The change in polarization yields the magnitude of the applied magnetic field. The pumping laser supplies multiple fiber optic cables and is thus used for multiple magnetometers. An array of these magnetometers for relaxometry measurements can comprise 7 vapor cells placed with one in the center surrounded by 6 more. The applied field from the magnetizing coils is perpendicular to the arrangement shown in FIG. 5 in order to induce the maximum observable magnetic moments into the nanoparticles. The photo at the bottom of FIG. 7 shows an exemplary physical arrangement and size of the atomic magnetometer for application with the present invention. The sensitivity of the device shown is 0.16 fT/√Hz, compared to sensitivity of an exemplary SQUID system as shown in FIG. 5 of 1.0 pT/√Hz (1000 fT/√Hz). Atomic magnetometers require no cryogenic coolant which can make them desirable for clinical applications where such coolants, in particular liquid helium, are not always readily obtainable.

Example Application to Detection of Breast Cancer.

For breast cancer, the current method of choice for screening and detection is mammography. While mammography has led to a significant improvement in our ability to detect breast cancer earlier, it still suffers from the inability to distinguish between benign and malignant lesions, difficulty in detecting tumors in dense and scarred breast tissue, and fails to detect 10-30% of breast cancers. The use of magnetic nanoparticles conjugated to tumor-specific reagents combined with detection of these particles through measurement of their relaxing fields represents a promising new technology that has the potential to improve our ability to detect tumors earlier. Furthermore, detection of targeted magnetic nanoparticles using weak field sensors is fast and is can be more sensitive than MRI detection because only particles bound to their target cells are detected.

We have developed conjugated magnetic nanoparticles targeted to breast cancer cells that express the HER2 antigen, which is overexpressed on ~30% of human breast cancers. We have characterized the nanoparticles for their magnetic properties and selected those of optimal size and magnetic moment per mg of Fe. A number of different cell lines that have specificity to HER2 have been studied to determine their site density and sensitivity of the sensor system for detection. A SCID mouse model was explored using tumors grown from human cell lines, imaging the mouse under the sensor system followed by confirming histology studies. These results indicate the validity of the magnetic sensor approach for sensitive detection of breast cancer.

Figure 8:
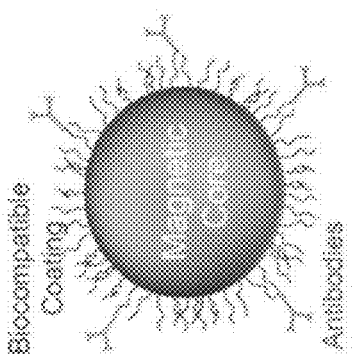
FIG. 8 is schematic illustration of a magnetic nanoparticle with biocompatible coating and attached antibodies for targeting specific cells.
Figure 9:
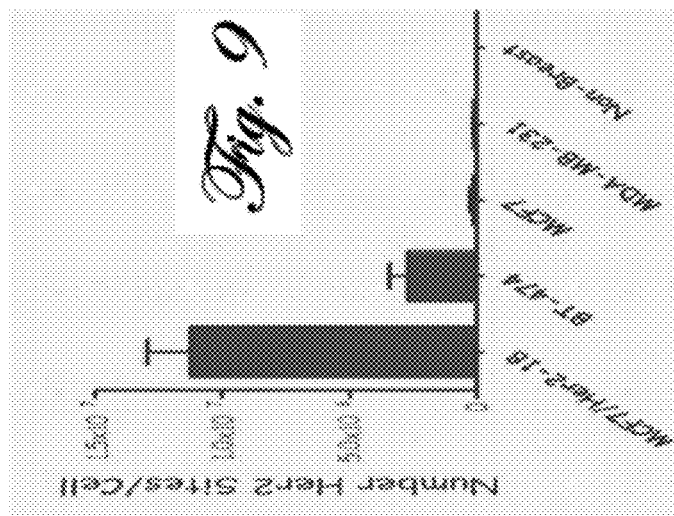
FIG. 9 is a depiction of the number of Her2 sites per cell calculated by comparison to a range of microspheres with known binding capacities.

FIG. 8 is schematic illustration of a magnetic nanoparticle with biocompatible coating and attached antibodies for targeting specific cells. In a demonstration of an example embodiment of the present invention, we used HER2 Antibodies (Ab) that are specific to 30-40% of breast cancers. The nanoparticles had coatings containing Carboxyl groups and a Sulfo-NHS method is used to conjugate the nanoparticles to the antibodies. Flow cytometry performed for breast cancer cell lines MCF7, MCF7/Her2-18 (MCF7 clone stably transfected with Her2), BT474, and MDA-MB-231. Number of Her2 binding sites determined by flow cytometry, Anti-Her2 antibodies conjugated to the fluorescent probe FITC. FIG. 9 is a depiction of the number of Her2 sites per cell calculated by comparison to a range of microspheres with known binding capacities. MCF7 cells engineered to overexpress Her2-18 have $11\times10^6$ Her2 binding sites/cell, BT-474 have $2.8\times10^6$, MCF7 $0.18\times10^6$, MDA-MB-231 $0.11\times10^6$ Non-breast cell lines have <4000 Her2 binding sites/cell.

Figure 10:
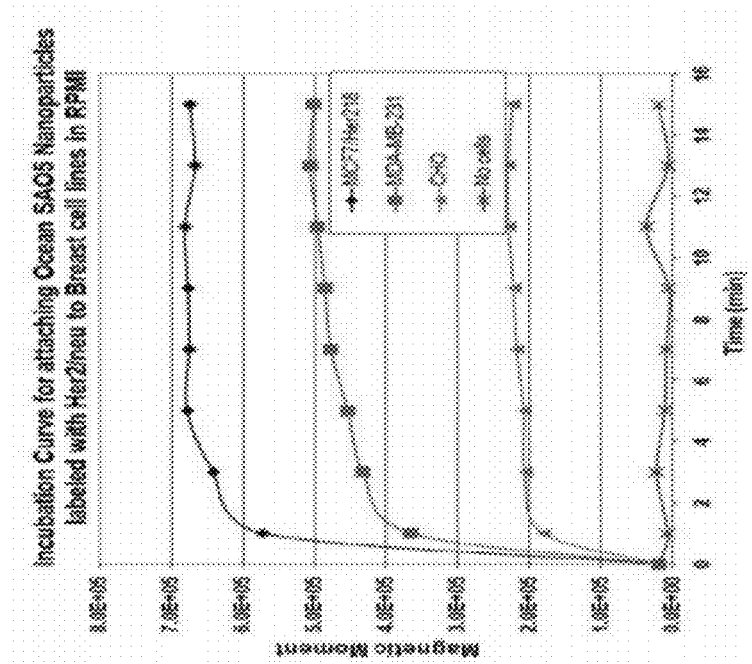
FIG. 10 is an illustration of magnetic moments of two breast cancer cell lines, MCF7/HER218 and MDA-MB-231 measured as function of time after incubating with HER2/neu antibodies and nanoparticles.

FIG. 10 is a graph of a measurement of the magnetic moment in the SQUID sensor system as a function of time for incubation of attaching magnetic nanoparticles (from Ocean Nanotech) to breast cancer cell lines. The magnetic nanoparticles were coated with a carboxyl biocompatible coating and were then conjugated to the Her2/neu antibody. This antibody is specific to approximately 30% of breast cancer cells in humans. The labeled magnetic nanoparticles were inserted into vials containing live cancer cells and the magnetic moments of the vial measured at various times ranging from one minute to 16 minutes. The zero time point is the magnetic moment of the vial of nanoparticles before adding to the cells. The lack of magnetic moment for the unmixed particles is a demonstration that unbound particles give no magnetic signal with this SQUID imaging method. Upon mixing with the cells, the magnetic moments increase rapidly and saturate indicating that the cells have collected on their surfaces the maximum number of nanoparticles possible in one to two minutes. The top curve is for the breast cancer cell line, MCF7/Her218 that is known to be very specific for the Her2/neu antibody and the large magnitude of the magnetic signal verifies this. The breast cancer cell line, MDA-MB-231, is also positive for Her2/neu but with much fewer sites for the antibody targeted nanoparticles to attach to. The smaller magnitudes are also indicative of this trend. The CHO cell line is non-specific to Her2/neu and gives substantially smaller magnetic moments after incubation. The presence of a magnetic moment is indicative of some phagocytosis of these cells where the nanoparticles enter the cells. The curve for no cells is for the vials containing nanoparticles only and shows that the particles alone continue to give no signal and thus there is no agglomeration occurring of the particles. These results demonstrate the specificity of the antibody for the target cancer cells and verify that only bound particles give magnetic moments. This result is not true for other methods such as MRI which sees all particles, bound or unbound.

Figure 11:
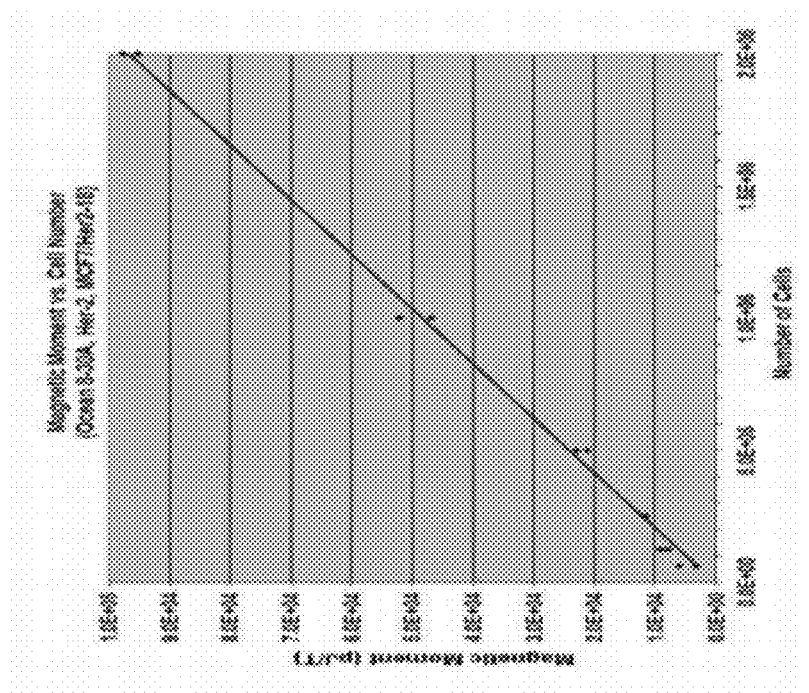
FIG. 11 is an illustration of the magnetic moments of cell samples measured as function of number of cells by pipetting cells down by factors of two.

FIG. 11 is an illustration of the magnetic moments of cell samples measured as function of number of cells by pipetting cells down by factors of two. The demonstrated sensitivity is 100,000 cells for MCF7 cells and Ocean nanoparticles, for cells 3.5 cm from the sensor. There are $2.5 \times 10^6$ np/cell. Linearity demonstrates magnetic moment yields # of cells; MRI contrast is not a linear function of cell number. A typical mammogram requires 10 million cells.

Figure 12:
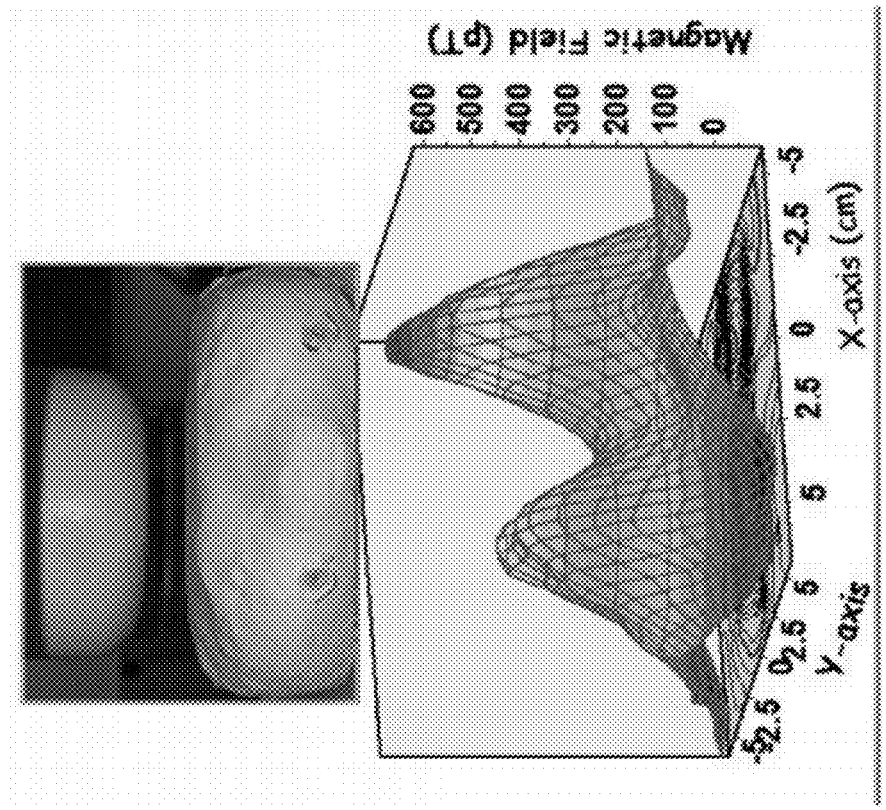
FIG. 12 is an illustration of a phantom with inserted vials of MCF7 Cells, left 2E+06, right=1E+06 cells.

A breast phantom was constructed using a standard mammogram calibration phantom as a model. The phantom was constructed out of clay, non-metallic material is transparent to these fields. Vials containing live cells were inserted into the phantom. FIG. 12 is an illustration of a phantom with inserted vials of MCF7 Cells, left $2 \times 10^6$, right=$1 \times 10^6$ cells. Cells conjugated to HER2 Ab, the np from Ocean Nanotech. Fields mapped at five 7-channel SQUID positions=35 sites. 3-D contour maps represent the field distributions. Locations and moment magnitudes obtained from inverse problem. Moments determine the number of cells in vials from cell data shown above.

Figure 14:
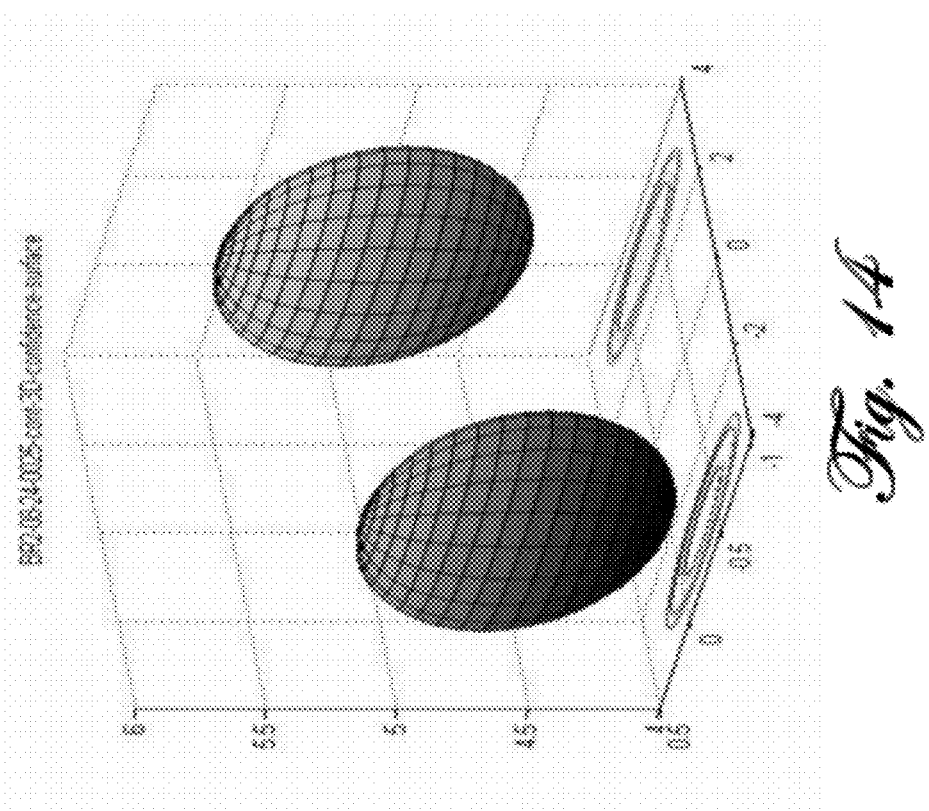
FIG. 14 contains position confidence plots obtained from mouse tumors.
Figure 13:
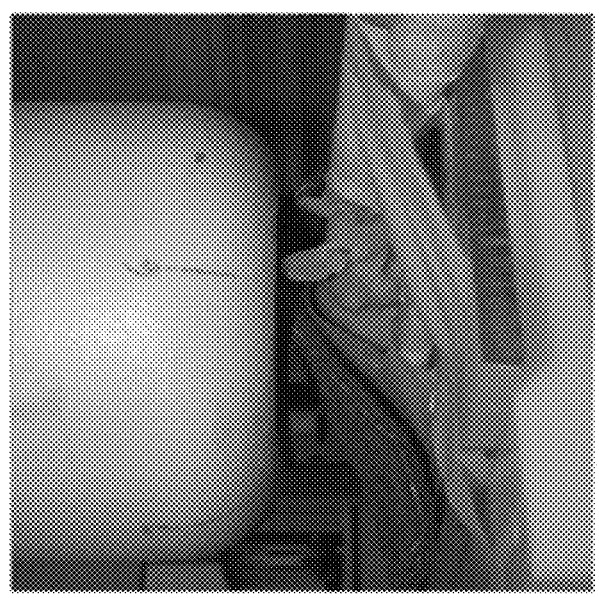
FIG. 13 is a photo of a nude mouse under a SQUID system.

A mouse model of breast cancer was developed appropriate for SQUID sensor measurements. SCID nude mice were used with xenograft human breast cancer cell lines. FIG. 13 is a photo of a nude mouse under a SQUID system. To study in-vivo processes by the SQUID technique, a mouse was injected with human MCF7 cells two weeks previously in two places. These cells then produced human tumors on the flanks of the mouse; one such tumor is visible behind the right ear of the mouse. The mouse was anesthetized through the tube over its mouth. Labeled magnetic nanoparticles were injected into the mouse at this stage either by tail, inter-peritoneal, or inter-tumoral injections. Subsequent to injections, the mouse was placed under the sensor system as shown and a magnetizing pulse was applied and the resulting magnetic moments of the injected particles were measured. As in the case of the live cancer cells, no moments were observed unless the particles had attached to cells within the tumors. In some cases both tumors were MCF7 type cells and in other cases, two different cell lines were used to develop the tumors in the mice. The mouse resided on the stage shown in FIG. 5 and could be moved to several positions under the sensor system to obtain more spatial information. Measurements were made as a function of time to determine how fast the particles were taken up from the blood stream and how fast phagocytosis occurred with the particles ending up in the liver. The mouse was typically placed at five stage positions under the 7-channel SQUID system to obtain 35 spatial locations. The magnetic fields at all positions were then used in a special code to solve the electromagnetic inverse problem using the Levenberg-Marquardt theorem to determine the location of all sources of magnetic particles in the mouse. This information was then compared to the known geometry of the mouse from photographs to determine the accuracy and sensitivity for locating breast cancer tumors in living animals. FIG. 14 contains position confidence plots obtained from mouse tumors. Left sphere is from left tumor that is ~2× right tumor in magnetic moment (see below). Positions calculated by two dipole least squares method to extract magnetic moments and positions. Moments determine number of labeled cells in tumors.

Figure 17:
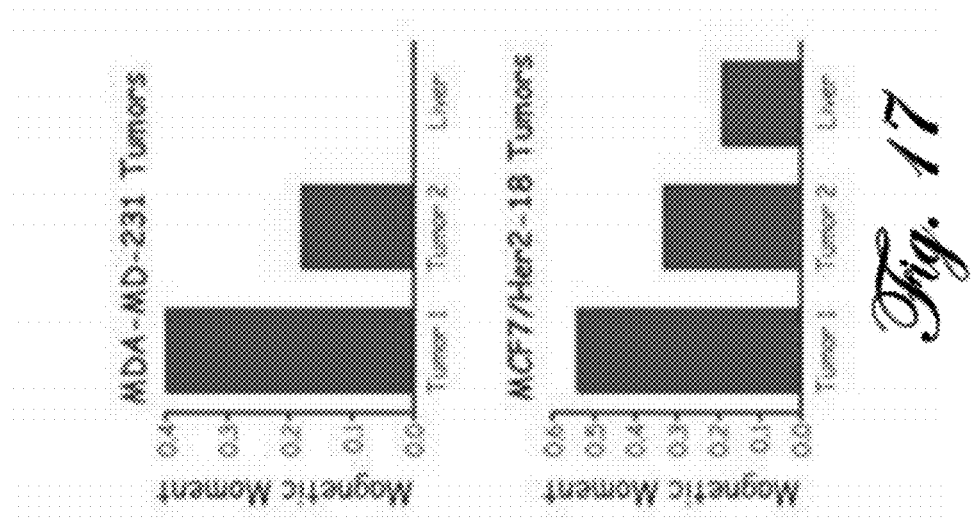
FIG. 17 is an illustration of the results of these measurements and show very good agreement with the in-vivo measurements on the live mouse.
Figure 16:
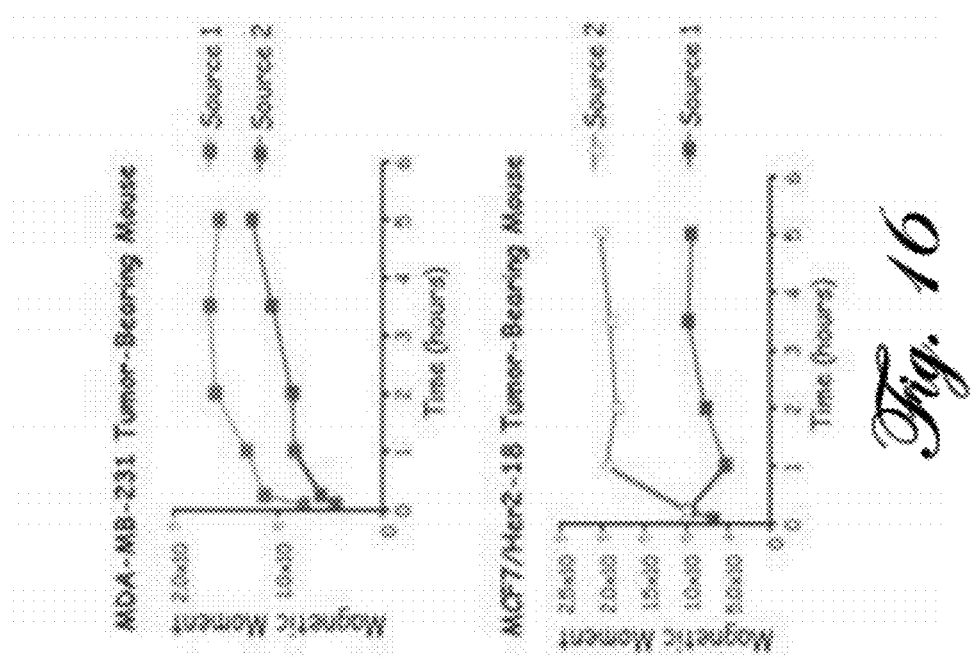
FIG. 16 is an illustration of the time course of the measurements for the two mice and both tumors of each mouse.
Figure 15:
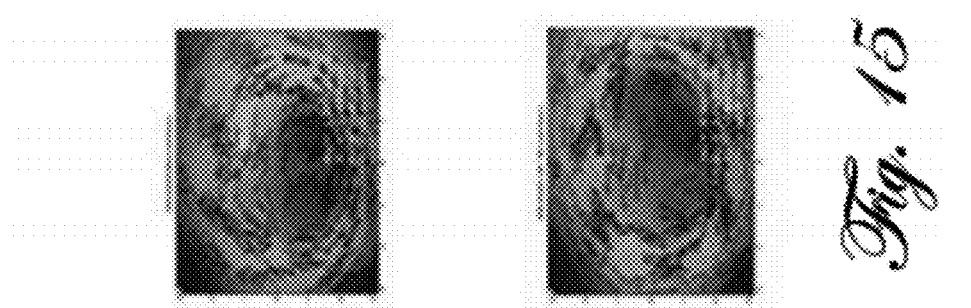
FIG. 15 is an illustration of the magnetic contour lines observed for 35 different measurement sites
Figure 18:
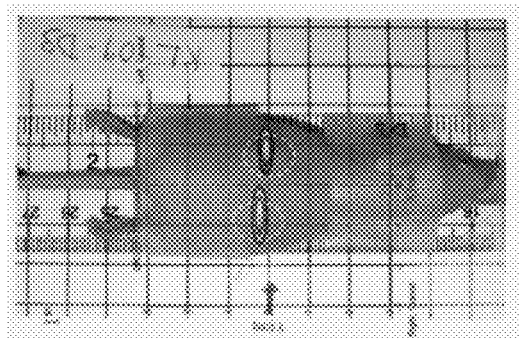
FIG. 18 is an illustration of the 2-dimensional 95% confidence limit for the locations of the two tumors superimposed on the actual tumors of the mouse.

The SQUID system results for in-vivo measurements on living animals are shown in FIGS. 16, 17, 18 for two different tumor bearing animals. Each mouse had two tumors but of different cell types. Different amounts of nanoparticles were absorbed by each of the two tumors. The mouse with MCF7 cells showed higher magnetic moments than the mouse with MDA-MB-231 tumors as expected due to the higher number of specific sites for HER2/neu antibodies on the former. FIG. 15 is an illustration of the magnetic contour lines observed for 35 different measurement sites as described in FIG. 13. Analysis of these magnetic fields yielded the spatial positions of the tumors that agreed with the measured values of these positions; the SQUID results giving higher precision than the physical measurements of approximately 3 mm. FIG. 16 is an illustration of the time course of the measurements for the two mice and both tumors of each mouse. The uptake of the particles occurred rapidly with the signal near maximum obtained in the first hour. The nanoparticles remain in the tumors for at least 5 hours, the length of the experiments. Subsequent to these measurements, the mice were euthanized and the tumors and other organs removed and placed under the sensor system to determine how much of the nanoparticle injections were in the tumors. The plots in FIG. 17 are illustrations of the results of these measurements and show very good agreement with the in-vivo measurements on the live mouse. In the lower left figure, a magnetic moment was observed in the liver indicating that some phagocytosis had occurred and the particles were delivered to the liver for elimination. Subsequent histology of the tumors also showed significant attachment of the particles to cells in the tumor using Prussian blue staining to emphasize the iron in the magnetic nanoparticles.

Figure 19:
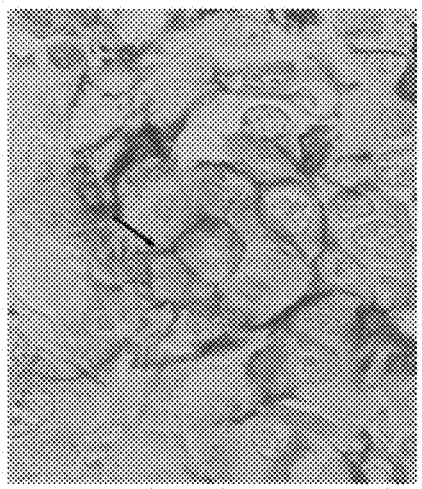
FIG. 19 is a photo of the histology of tumors after extraction.

Confidence regions were calculated for determining the accuracy of location of tumors for the in-vivo measurements of the mice. FIG. 18 is an illustration of the 2-dimensional 95% confidence limit for the locations of the two tumors superimposed on the actual tumors of the mouse. An accuracy of spatial location of approximately +/−3 mm is obtained in the x and y direction. FIG. 19 is a photo of the histology of tumors after extraction. Microscopic image of one MCF-7 tumor slice. Prussian Blue staining of cells reveals iron present in np attached to cells. Arrow points to cell covered with np.

A sensitive magnetic field sensor system has been demonstrated for in-vivo early detection of breast cancer by detecting magnetic nanoparticles, conjugated to antibodies for breast cancer cell lines. Hundreds of thousands of nanoparticles attach to each cancer cell. Method is sensitive to <100,000 cells at distances comparable to breast tumors. Standard x-ray mammography requires typically cell density of ten million cells. Measured moments are linear with cell number; i.e. measure of magnetic moment yields the number of cancer cells present. Very high contrast-nanoparticles not attached to cells are not observed. Phantom studies demonstrate multiple sources are localized accurately and number of cells per source determined. Mouse model was developed using multiple tumors of human breast cancer cell lines and in-vivo measurements made to determine the location and cancer cell count of these tumors subsequent to nanoparticle injections. Solutions of the inverse problem successfully locate tumors and number of cells. Histology confirms presence of np mouse tumors.

Example Application to Detection of Ovarian Cancer.

The etiology of ovarian cancer is not well understood and there is little evidence for risk factors suggesting preemptive screening. The normal screening test is pelvic examination if there are suspected symptoms, such as abdominal enlargement, and the results typically reveal advance stage of cancer. Routine screening of women presently is not done as there are no reliable screening tests. The great difficulty now with ovarian cancer is that by the time it is detected, it has metastasized from the ovary into other organs. For this reason, a hysterectomy is often performed along with the ovary removal. If the presence of ovarian cancer can be identified early and is contained in the ovary, the five year survival rate is 95%. However, only 29% are detected at this stage. If the disease has spread locally, this survival rate drops to 72% and if metastasized to distant locations, the rate of survival is 31%. Thus, development of early detection methods is imperative.

Figure 20:
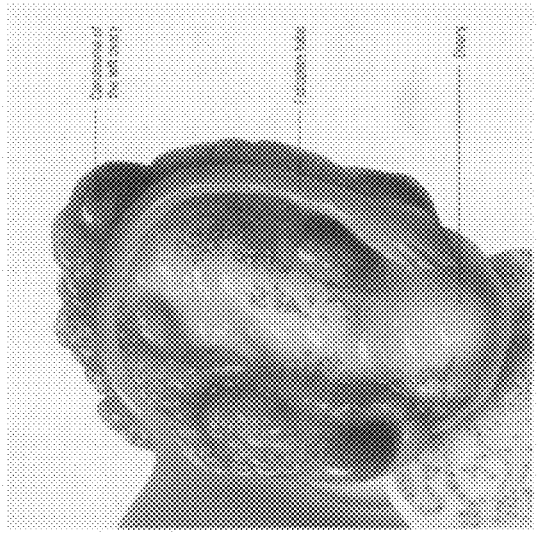
FIG. 20 is an illustration of an ovarian cancer showing the growth of the tumor on the ovary.
Figure 21:
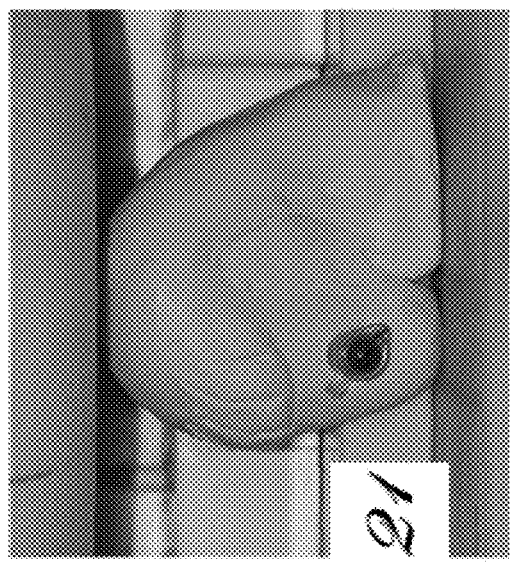
FIG. 21 is photograph of a full-size ovarian phantom placed under a SQUID sensor apparatus at a distance that would be typical of a patient subject.

FIG. 20 is an illustration of an ovarian cancer showing the growth of the tumor on the ovary. These tumors consist of cells with high numbers of receptors for the antibody CA-125 and can be targeted with magnetic nanoparticles labeled with this antibody. FIG. 21 is photograph of a full-size ovarian phantom placed under a SQUID sensor apparatus at a distance that would be typical of a patient subject. The phantom has a vial containing live ovarian cancer cells inserted into it. Magnetic nanoparticles labeled with the antibody CA-125 were inserted into this vial and because these antibodies are highly specific for these ovarian cancer cells, large numbers became attached to the cell surface. These magnetic nanoparticles were then detected by the SQUID sensor apparatus to provide sensitivity calibrations for in-vivo measurements for both animal and human in-vivo models.

The results of the sensitivity studies for live ovarian cells inserted into the phantom shown in FIG. 21 are illustrated in FIG. 22 for three different ovarian cancer cell lines; namely, tov-112D, Ov-90, and nihovcar-3. The plot shows the minimum number of cells that were detected by this apparatus for the three different cell lines as a function of distance from the sensor to the patient's ovaries. The cancer cell line ov-90 is known to be one of the most aggressive of the cancers and these results indicate that there are many receptors for CA-125 on the surface of the cell. The number of nanoparticles per cell can be estimated from these measurements and corresponds to 20,000 particles per cell for tov-112D, 3400 for ov-90, and 6700 for ovcar-3.

FIG. 23 is an illustration of confirmation of antibody sites for these cells using flow cytometry. FIGS. 23a and 23b show two of the four cell lines examined. The signal from cells only is shown and the isotype (using a non-specific binding molecule, Igg), the Her2/neu antibody, and CA-125 antibody are shown with increasing site number to the right on these plots. These figures show that the CA-125 antibody has a large number of sites on these cells, with SK-OV-3 the largest of these two. The antibody Her2/neu is also specific to 30% of breast cancer cells.

Figure 24:
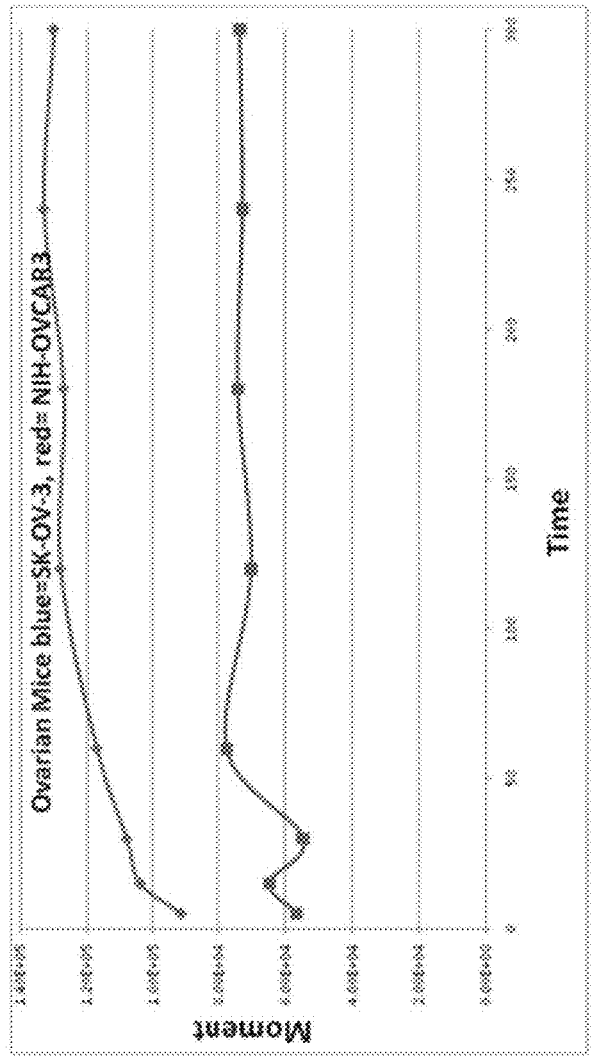
FIG. 24 is an illustration of magnetic moments from magnetic nanoparticles (from Ocean Nanotech) attached to ovarian human cancer tumors in the live mouse.

Measurements were made as a function of time to determine how fast the particles were taken up from the blood stream and how fast phagocytosis occurred with the particles ending up in the liver. Measurement of the magnetic moment in the SQUID sensor apparatus as a function of time for magnetic moments from magnetic nanoparticles (from Ocean Nanotech) attached to ovarian human cancer tumors in the live mouse is shown in FIG. 24. The mouse had two ovarian tumors, one of SK-OV-3 and the other of NIH-OVCAR3. The magnetic nanoparticles were coated with a carboxyl biocompatible coating and were then conjugated to the CA-125 antibody. This antibody is specific to ovarian cancer cells in humans. The labeled magnetic nanoparticles were injected into the mouse tumors and the magnetic moments of the mouse measured at various times ranging from one minute to 300 minutes. The uptake of the particles occurred rapidly with the signal near maximum obtained in the first hour. The time course indicates that the nanoparticles remain in the tumors for a number of hours. The nanoparticles remained in the tumors for at least 5 hours, the length of the experiments. Different amounts of nanoparticles were absorbed by each of the two tumors. The mouse tumor with SK-OV-3 cells showed higher magnetic moments than the mouse with NIH-OVCAR-3 tumors, as expected due to the higher number of specific sites for CA-125 antibodies on the former. The nanoparticles gave no magnetic moment before injection and only yield a magnetic signal when attached to something such as the cells in the tumor. Experiments have shown that injections into sites other than the tumor do not yield a signal as the particles do not bind to normal cells. After a period of time, the liver begins to show signs of accumulation of these particles as they are phagocytised from the system. Subsequent to these measurements, the mice were euthanized and the tumors and other organs removed and placed under the sensor apparatus to determine how much of the nanoparticle injections were in the tumors. These measurements agreed very well with the in-vivo measurements on the live mouse. Subsequent histology of the tumors showed significant attachment of the particles to cells in the tumor using Prussian blue staining to emphasize the iron in the magnetic nanoparticles.

A photograph of a mouse used to verify that the SQUID sensor method works in-vivo along with magnetic contour fields from this mouse are shown in FIG. 25. Human xenograft tumors are shown on the flanks of the mouse; these are the bumps above and to both sides of the tail in FIG. 25. These tumors were produced by injecting live human ovarian cancer cells into this severely-compromised-immune-deficient mouse and allowed to grow for several weeks until a 6-10 mm tumor was evident. The mouse was anesthetized through the tube over its mouth during all SQUID sensor experiments. Labeled magnetic nanoparticles were injected into the mouse at this stage either by tail, inter-peritoneal, or inter-tumoral injections. Subsequent to injections, the mouse was placed under a sensor as shown in FIG. 1 and a magnetizing pulse was applied and the resulting magnetic moments of the injected particles was measured. As in the case of the live cancer cells, no moments were observed unless the particles had attached to cells within the tumors. In some cases both tumors were SK-OV-3 type cells and in other cases, two different cell lines were used to develop the tumors in the mice.

The mouse placed on the stage shown in FIG. 5 could be moved to several positions under the sensor to obtain more spatial information. The mouse was typically placed at five stage positions under a 7-channel SQUID to obtain 35 spatial locations. The magnetic fields at all positions were then used in a code to solve the electromagnetic inverse problem using the Levenberg-Marquardt theorem to determine the location of all sources of magnetic particles in the mouse. This information was then compared to the known geometry of the mouse from photographs to determine the accuracy and sensitivity for locating cancer tumors in living animals. FIG. 25 shows the magnetic contour lines observed for 35 different measurements. Analysis of these magnetic fields yielded the spatial positions of the tumors that agreed with the measured values of these positions; the SQUID results giving higher precision than the physical measurements of approximately 3 mm.

Example Application to Detection of Hodgkin's Lymphoma.

Hodgkin's lymphoma (HL) accounts for 30% of all lymphomas. HL characteristically arises in lymph nodes, preferentially in the cervical regions, and thymus; but in advanced disease can involve distant lymph nodes, the spleen, and bone marrow. The majority of cases are in young adults between 15 and 34, but a second incidence peak occurs in people over 55. Currently, biopsy evaluation is required for diagnosis. Surgical biopsy has complications, such as infection and bleeding, and the evaluation of the biopsy typically takes 3-5 days. Thus, in HL cases in which the tumor mass is preventing blood return to the heart (i.e., superior vena cava syndrome, 10% of cases), significant morbidity or mortality can occur during this waiting period. Several of the antibodies that target Hodgkin's lymphoma; namely CD15, CD30, and CD25 have been identified. The latter antibody, however, targets many cells and is less specific. Another application where the present invention can have significant clinical impact is in the detection of persistent HL after therapy. If a patient experiencing a relapse undergoes high-dose radiation therapy, there is a good prognosis if the relapse is detected early. Patients who have a relapse will have a prognosis determined primarily by the duration of the first remission. The persistence of large fibrotic nodules, particularly in the mediastinum, after therapy leads to uncertainty in the determining whether persistent cancer is present and surgery of fibrotic nodules is fraught with difficulty to control bleeding problems and patient morbidity.

The relaxometry method of the present invention can provide a quantitative estimation of the number of lymphoma cells present in organs affected by Hodgkin's disease, such as the thymus and spleen. The RS cells are giant cells derived from B-lymphocytes that contain millions of receptors for CD30 and CD15. Previous results with SQUID sensors targeting T-cell lymphocytes have shown that for smaller cells, approximately a million nanoparticles can be attached to each T-cell. Steric hindrance limits the number of nanoparticles attached to a normal lymphocyte but the much larger RS cells can have 25 to 50 times more bound nanoparticles. The amount of iron per nanoparticle is $4.4 \times 10^{-6}$ ng/np. Given the large size of the RS cells, there can be several million nanoparticles per cell so that each cell may have up to 10 ng of iron. One hundred RS cells accumulated in the spleen or thymus can contain a microgram of iron. Less than a microgram is adequate for SQUID detection, therefore a detectability of 100 RS cells is possible. The measured amplitude of the residual magnetization of the antibody-labeled nanoparticles in vivo can provide an important diagnostic tool in lymphoma cancer. The signal strength depends on the density of antigens on the tumor cell surfaces and thus the field strength produced by the nanoparticles is proportional to the number density of antigenic sites on lymphoma cells. Particle number and density can be determined to provide the amplitude of the detected magnetic field. This information can be used in planning in vivo detection, as well as for assisting in the choice of nanoparticles to be used. The SQUID sensor is an ideal sensor system for Hodgkin's disease with large sensitivity for RS cells and in-vivo detection of the disease without biopsies and the ability to monitor the treatment of the disease during chemotherapy.

FIG. 26 is a graph of a measurement of the magnetic moment in a SQUID sensor system as a function of time for incubation of attaching magnetic nanoparticles (from Ocean Nanotech) to lymphoma cell lines. The magnetic nanoparticles were coated with a carboxyl biocompatible coating and were then conjugated to the CD34 antibody. This antibody is specific to one type of lymphoma cells, namely, Acute Lymphomatic Leukemia in humans. The labeled magnetic nanoparticles were inserted into vials containing live cancer cells and the magnetic moments of the vial measured at various times ranging from one minute to 16 minutes. The zero time point is the magnetic moment of the vial of nanoparticles before adding to the cells. The lack of magnetic moment for the unmixed particles at time zero shows that unbound particles give no magnetic signal with this SQUID imaging method. Upon mixing with the cells, the magnetic moments increase rapidly and saturate indicating that the cells have collected on their surfaces with the maximum number of nanoparticles possible in one to two minutes. The top curve is for the lymphoma cancer cell line U937 that is known to be very specific for the CD34 antibody and the large magnitude of the magnetic signal verifies this. The lower curve is for the same cell line but a non-specific marker, BSA, and shows substantially smaller magnetic moments after incubation. The presence of a magnetic moment for the BSA is indicative of some phagocytosis of these cells where the nanoparticles enter the cells. U937 is a lymphoma of the T lymphocyte cells and RS is a lymphoma of the B lymphocyte cells. Since one of the principle purposes of lymphocyte cells is to take up particles that do not belong, this amount of non-specificity is expected. These results demonstrate the specificity of the antibody for the target cancer cells and verify that only bound particles give magnetic moments. This result is not true for other methods such as MRI which sees all particles, bound or unbound.

Samples of RS cells were obtained from the Tissue Bank facility at the University of New Mexico, a nationally recognized institution for cell banking and quantity of specimens. The efficiency of the SQUID sensor system for detecting RS cells was compared to the number of RS cells in a sample determined by manual hematocytometer counts. These isolated RS cells were labeled with nanoparticles specificity bound to CD15 and CD30 during the isolation procedure. Calibration of sensitivity was performed by serially dilution over a range of 1 in 10 to 1 in 100,000 cells. Ranges of nanoparticle density on malignant cells exceed 107 nanoparticles/cell. The site density of CD15 is determined using a flow cytometry technique that quantifies receptors/cell. The number of CD15 and CD30 sites/cell was confirmed using a quantitative immunofluorescence staining technique.

FIG. 27 is an illustration of the results of the flow cytometric measurements of RS cells from the lymphatic system in determining the number of sites available for nanoparticles and detection by the SQUID sensors. FIG. 27A is a photograph showing the morphologic appearance of RS cells isolated from a lymph node specimen. FIG. 27B shows the flow cytometric analysis of a bone marrow sample where (B1) is before and (B2) after performing an enrichment procedure to enhance the frequency of RS cells in a sample for flow cytometry. Normally RS cells occur at a frequency of 1 in $10^4$ or $10^5$ of normal lymphocyte cells and must be enhanced before using CD15 and CD30 staining by flow cytometry in order to be detected. The SQUID sensor system detects all of the RS cells in-vivo and does not require sampling so enhancement is not necessary, as is required in the flow cytometry determinations.

The lymph nodes are one of the primary sites where RS cells accumulate, aside from the thymus gland. FIG. 28 is a histology slice from a patient with Hodgkin's Disease. The RS cells have been stained with immunoperoxidase staining. The antibody CD15 is shown on the right and the antibody CD30 on the left. The surrounding cells are non-malignant cells in the lymph node. The SQUID sensor can detect several hundred of these labeled RS cells in a lymph node.

Example Application to Detection and Staging of Prostate Cancer.

Prostate cancer has a high mortality rate due to the lack of early detection with standard screening technologies. The number of cases for 2009 in the US was 192,280 with 27,360 deaths. Prostate cancer accounts for 9% of male deaths and there is a 1 in 6 lifetime probability for developing prostate cancer. The disease is normally undetected until it has caused an enlargement of the prostate, urinary problems, or has spread to other organs. Asymptomatic detection of the disease is normally done by a digital examination, an elevated PSA test result, or a biopsy. The PSA test is now considered unreliable causing many unnecessary biopsies with accompanying dangers of infection. The digital examination is also highly subjective. Testing for prostate cancer is very controversial. The cost of PSA tests in the US alone exceed $3 billion and a recent study reported in the New England Journal of Medicine found that current screening methods do not reduce the death rate in men over 55 years old. The present invention can detect this cancer before it has metastasized.

An exemplary method to detect prostate cancer in a tissue comprises placing the patient on a measurement stage of a superconducting quantum interference device sensor apparatus; injecting a plurality of antibody-labeled magnetic nanoparticles into the patient for specific binding to the tissue in the patient; applying a uniform magnetizing pulse field to magnetize the nanoparticles injected into the patient; and detecting the residual magnetic field of the magnetized nanoparticles thereby providing an image of the nanoparticles bound to the tissue of the patient. The tissue can comprise prostate tissue and the antibody-labeled magnetic nanoparticles can specifically bind to antigens of prostate cancer cells. The antibody-labeled magnetic nanoparticle can comprise a magnetic core coated with a biocompatible coating to which is attached specific antibodies. For example, the magnetic core can comprise a ferromagnetic material, such as iron oxide. For example, the biocompatible coating can comprise Dextran, carboxyl, or amine. For the detection of prostate cancer, the specific antibody can be PSMA antibody.

The prostate-specific membrane antigen (PSMA) is a transmembrane glycoprotein that is highly expressed by most prostate cancers. It is also referred to as mAb 7E11. It is expressed on the surface of the tumor vascular endothelium of solid carcinomas but not on normal prostate cells. The amount of PSMA observed in prostate cancer follows the severity or grade of the tumor. Flow cytometry has shown that there are large numbers of receptor sites for this antibody on several cell lines of prostate cancer including LNCaP and PC-3, whereas a PSMA negative cell line, DU-145 indicates no expression. Results of attaching magnetic nanoparticles to these positive cell lines demonstrate one million or more nanoparticles per cell. These results are comparable to results from ovarian and breast cancer regarding nanoparticles per cell and depths of tumors in the body, and biomagnetic detection methods using SQUID sensors will have the same sensitivity for prostate cancer as ovarian cancer (described in one or more of the related applications incorporated by reference above). Results of studies on ovarian cancer can thus be directly applied to prostate cancer detection and localization. Compared to the CA-125 antibody for ovarian cancer, the PSMA is even more specific for in vivo prostate specific targeting strategies.

Figure 29:
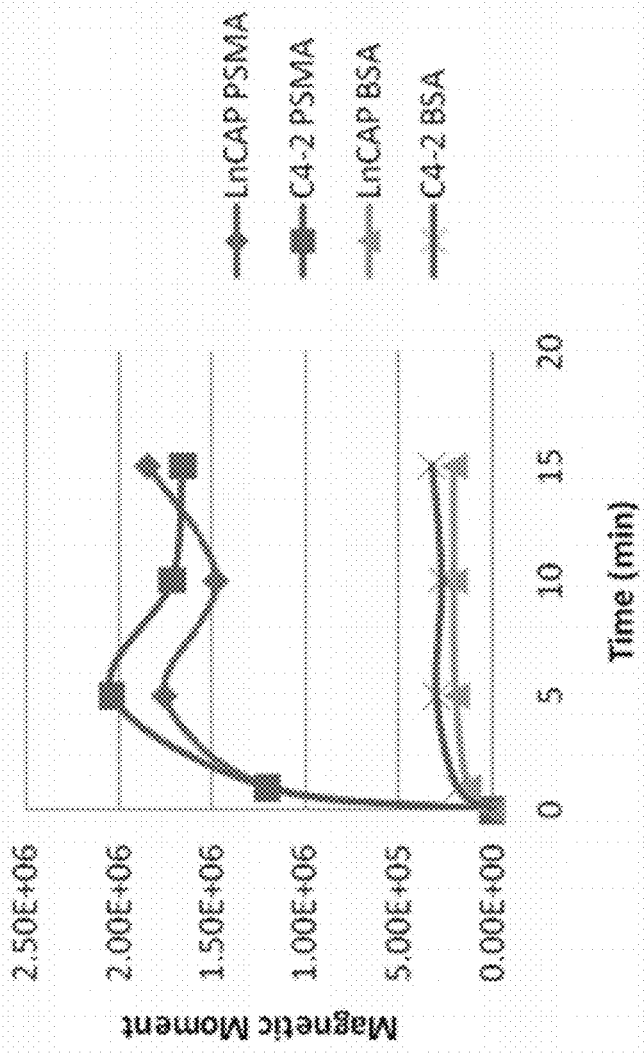
FIG. 29 is a schematic illustration of results obtained from measuring, with an embodiment of the present invention, prostate cancer cells with PSMA targeted nanoparticles.

The measurement of prostate cancer cells using an embodiment of the present invention was verified experimentally, as illustrated in FIG. 29. LnCAP and C4-2 are prostate cancer cell lines that are positive for PSMA. 3 million cells of each of these cell lines were exposed to anti-PSMA coated Ocean nanoparticles and BSA coated Ocean nanoparticles. BSA serves as a negative control. As can be seen from the figure, the magnetic moment measured by the SQUID instrumentation is much higher for the PSMA-targeted nanoparticles than for the control nanoaprticles.

The SQUID sensor method can provide a quantitative estimation of microvascular structure in tumors leading to a new surrogate for vessel formation (angiogenesis) and individual tumor gradation. It has been shown in a study of tumor microvascular characterization in an experimental prostate cancer model using nanoparticles that tumor growth and aggressiveness/grade have a direct relationship to tumor neovascularization. Other studies estimate the concentration of magnetic particles in a tumor to be about 2.3 mg of nanoparticles per gram of tissue. This concentration is regularly achieved in the tumors of human liver cancer patients receiving treatment via intrahepatic arterially administered radioactive microspheres; the nanoparticles tend to concentrate in the vascular growth ring of a tumor. Less than a nanogram is adequate for SQUID detection. The measured amplitude of the residual magnetization of the antibody-labeled nanoparticles in vivo can provide an important diagnostic tool in prostate cancer. The signal strength depends on the density of antigens on the tumor cell surfaces and thus the field strength produced by the nanoparticles is proportional to the number density of antigenic sites on prostate tumor cells. Thus, particle number and density provides the amplitude of the detected magnetic field. This information can then be used in planning in vivo, as well as for assisting in the choice of nanoparticles to be used.

Example Application to Detection of Glioblastoma.

Brain cancer is particularly deadly and occurs in a number of forms. Cancer involving the glial cells is the most prevalent form and also the most aggressive brain tumor in humans. Various glial cells may be involved causing cancer of the type oligodendroglioma (involving the oligodendrocytes), astrocytoma (involving the astrocytes) and glioblastoma. The latter is the most frequently occurring of the brain cancers. These types of cancer normally results in death within a very short period of time. Gliablastoma cells can be targeted by markers such as EGFR, 8106, and PTN antibodies that may be used to image this type of cancer. Mouse models and brain cancer cell lines, such as U-251, are available for testing before human applications.

An important consideration in targeting brain cancer is the delivery across the blood brain barrier of the nanoparticles with markers attached. This barrier is somewhat opened in the vascular system associated with malignant tumors but still remains an impediment. The use of nanoparticles coated with lipophilic surfaces and then conjugated to antibodies or peptides increases the ability to cross the barrier. Additionally, the nanoparticle with markers can be encapsulated in a polymer coating with a liposome surface of in a micelle is another approach and releasing the conjugated nanoparticles from the polymer once inside of the brain using a slight application of a heating RF or ultrasound pulse.

An exemplary method to detect brain cancer comprises placing the patient on a measurement stage of a superconducting quantum interference device sensor apparatus; injecting a plurality of antibody-labeled magnetic nanoparticles into the patient for specific binding to the brain tumor in the patient; applying a uniform magnetizing pulse field to magnetize the nanoparticles injected into the patient; and detecting the residual magnetic field of the magnetized nanoparticles thereby providing an image of the nanoparticles bound to the tissue of the patient. The target is a brain tumor and the antibody-labeled magnetic nanoparticles can specifically bind to antigens of brain cancer cells. The antibody-labeled magnetic nanoparticle can comprise a magnetic core coated with a biocompatible coating to which is attached specific antibodies. For example, the magnetic core can comprise a ferromagnetic material, such as iron oxide. For example, the biocompatible coating can comprise Dextran, carboxyl, or amine. For the detection of glioblastomas, the specific antibody can be EGFR or similar antibody.

Angiogenesis EGFR has several forms and is a version of the epidermal growth factor receptor (EGFR) that is overexpressed by several types of cancer cells including glioblastoma cells and not normal cells. EGFR is currently undergoing immunotherapy clinical trials for patients with diagnosed glioblastoma. It can be conjugated with magnetic nanoparticles suitable for magnetic relaxometry detection and injected into the body. These magnetic nanoparticles can comprise a coating, such as polyethylene glycol (PEG), that will increase the efficacy of the targeted nanoparticles for penetrating the blood brain barrier. In another example embodiment of the present invention, the magnetic nanoparticles with markers attached can be contained within polymer coatings that are able to penetrate through the blood brain barrier and then released upon the application of a small RF heating pulse or the use of ultrasound. Results of attaching these angiogenesis peptides to magnetic nanoparticles and attaching these to cells are comparable to the use of other antibody results from ovarian and breast cancer regarding nanoparticles per cell and depths of tumors in the body. Biomagnetic detection methods using systems such as SQUID sensors will have the same sensitivity for brain cancer as ovarian cancer (described in one or more of the related applications incorporated by reference above). Results of studies on breast and ovarian cancer can thus be directly applied to brain cancer detection and localization.

Example Application to Detection of Pancreatic Cancer.

A number of tumor markers are present in pancreatic cancer. CA19-9 is one example of a marker that is elevated in this cancer but is not very sensitive (77%) and non-specific (87%). Combinations of markers have been suggested by the M.D. Anderson Cancer Center and these are being tested for screening of pancreatic cancer. These markers are microRNAs and include miR-21, MiR-210, miR-155 and miR-196a. However, this combination also only achieves a low sensitivity (64%) but a higher specificity (89%) than the CA19-9. In addition, a number of antibodies have been identified against certain cell lines of human pancreatic cancer, for example the FG cell line and these include S3-15, S3-23, S3-41, S3-60, S3-110, and S3-53. Another marker is muc1pan4 that is shown to be expressed in over 90% of pancreatic cancers. Another identifying marker is the urokinase plasminogen activator receptor (uPAR) that is highly expressed in pancreatic cancer and also in tumor stromal cells. The latter marker has been used to deliver magnetic nanoparticles to pancreatic cancers grown as xenografts in nude mice. These markers have led to MRI detection of the tumors in the mice when used as labeled contrast agents. The mechanism is primarily delivery of the nanoparticles to the tumor endothelial cells.

There are no reliable imaging approaches for diagnosis of pancreatic cancer. Thus the development of biomarkers as a targeted imaging agent for MRI, or permitting the more sensitive technique of magnetic relaxometry, is a significant advance. MRI can detect small abnormalities in tumors and is also useful in determining if cancer has metastasized. Dynamic Contrast Enhanced (DCE) MRI potentially distinguishes between benign and cancerous tumors but produces a number of false positives. The expense of MRI limits its application as a screening tool. MRI imaging of tumors often uses magnetic nanoparticles as contrast agents as mentioned above and is an accepted protocol providing standards for the injection of such nanoparticles. Intravascular MRI contrast agents at a dose of 2 mg/kg of nanoparticle weight have been used to detect metastatic lesions. However, the use of MRI in pancreatic cancer is severely limited.

The present invention can provide a quantitative estimation of microvascular structure in tumors leading to a new surrogate for vessel formation (angiogenesis) and individual tumor gradation. It has been shown in results in a study of tumor microvascular characterization in an experimental pancreatic cancer model using nanoparticles that tumor growth and aggressiveness/grade have a direct relationship to tumor neovascularization. Other studies estimate the concentration of magnetic particles in a tumor of ~2.3 mg of nanoparticles per gram of tissue. This concentration is regularly achieved in the tumors of human liver cancer patients receiving treatment via intrahepatic arterially administered radioactive microspheres; the nanoparticles tend to concentrate in the vascular growth ring of a tumor. Nanograms are adequate for detection by the present invention. The measured amplitude of the residual magnetization of the antibody-labeled nanoparticles in vivo can provide an important diagnostic tool in pancreatic cancer. The signal strength depends on the density of antigens on the tumor cell surfaces and thus the field strength produced by the nanoparticles is proportional to the number density of antigenic sites on pancreatic tumor cells. Particle number and density can be determined to provide the amplitude of the detected magnetic field. This information can be used in planning in vivo detection, as well as for assisting in the choice of nanoparticles to be used. Examples of pancreatic cancer cell lines include FG or MIA PaCa-2 that are known to be specific for the uPAR antibody.

The present invention has been described as set forth herein in relation to various example embodiments and design considerations. It will be understood that the above description is merely illustrative of the applications of the principles of the present invention, the scope of which is to be determined by the claims viewed in light of the specification. Other variants and modifications of the invention will be apparent to those of skill in the art.

What is claimed is:

1. A method of determining the presence, location, quantity, or a combination thereof, of one or more biological substances, comprising:
    (a) exposing a sample to a plurality of targeted nanoparticles, where each targeted nanoparticle comprises a paramagnetic nanoparticle conjugated with one or more targeting agents that preferentially bind with at least one of the biological substances, under conditions that facilitate binding of at least one of the targeting agents to at least one of the one or more biological substances;
    (b) subjecting the sample to a magnetic field of sufficient strength to induce magnetization of the nanoparticles;

(c) measuring a magnetic field of the sample after decreasing the magnetic field applied in step b below a threshold;

(d) fitting a decay curve of the magnetic field as measured over a period of time to a log/exponential function to determine the magnetic field of the sample at the time the magnetic field was decreased in step c to determine the presence, location, quantity, or a combination thereof, of the one or more biological substances from the magnetic field measured in step c.

2. A method as in claim 1, wherein the nanoparticles comprise iron oxide particles having a diameter of about 24 nm, or iron platinum particles having a diameter of about 15 nm.

3. A method as in claim 1, wherein the magnetic field in step b is applied with sufficient strength and for sufficient time to align the magnetic moments of at least 50% of the nanoparticles.

4. A method as in claim 1, wherein the magnetic field in step b has a strength of at least 50% of that required to completely saturate the magnetization of the nanoparticles.

5. A method as in claim 1 wherein the magnetic field in step b is applied with sufficient strength and for sufficient time to align the magnetic moments of more than 95% of the nanoparticles.

6. A method as in claim 1, wherein measuring the magnetic field in step c comprises using one or more superconducting quantum interference devices to measure the magnetic field.

7. A method as in claim 1, wherein measuring the magnetic field in step c comprises using one or more atomic magnetometers to measure the magnetic field.

8. A method as in claim 1, wherein measuring the magnetic field in step c comprises using one or more magnetic sensors coupled to one or more second order gradiometers to measure the magnetic field.

9. A method as in claim 1, wherein measuring the magnetic field in step c comprises using a plurality of magnetic sensors to measure the magnetic field, including measuring spatial characteristics of the magnetic field.

10. A method as in claim 9, wherein step d comprises determining a spatial distribution of the nanoparticles.

11. A method as in claim 1, wherein step d comprises solving an inverse electromagnetic problem to determine locations of magnetic sources in the sample.

12. A method as in claim 1, further comprising repeating steps b through d a plurality of times and averaging the magnetic field measurement in step c, the presence, location, quantity, or a combination thereof, of the one or more biological substances determined in step d, or a combination thereof, of two or more of such repetitions of steps c through d.

13. A method as in claim 1, wherein measuring the magnetic field in step c comprises measuring the magnetic field over a period of time.

14. An apparatus for the determination of the presence, location, quantity, or a combination thereof, of one or more biological substances, comprising:

a) a magnetization system, configured to subject a sample to a magnetic field, wherein the sample has been exposed to a plurality of targeted nanoparticles, where each targeted nanoparticle comprises a paramagnetic nanoparticle conjugated with one or more targeting agents that preferentially bind with at least one of the biological substances, under conditions that facilitate binding of at least one targeting agent to at least one of the one or more biological substances; wherein the magnetic field has sufficient strength to induce magnetization of the nanoparticles;

b) a magnetic measurement system, configured to measure a magnetic field of the sample after a magnetic field applied by the magnetization system has been decreased below a threshold;

c) an analysis system, configured to fit a decay curve of the magnetic field as measured by the magnetic measurement system over a period of time to a log/exponential function to determine the magnetic field of the sample at the time the magnetic field was decreased to determine the presence, location, quantity, or a combination thereof, of the biologic substance from the magnetic field measured by the magnetic measurement system.

15. An apparatus as in claim 14, wherein the magnetic measurement system comprises one or more superconducting quantum interference devices.

16. An apparatus as in claim 14, wherein the magnetic measurement system comprises one or more atomic magnetometers.

17. An apparatus as in claim 14, wherein the magnetic measurement system comprises one or more magnetic sensors coupled to one or more second order gradiometers.

18. An apparatus as in claim 14, wherein the magnetic measurement system comprises a plurality of magnetic sensors configured to measure spatial characteristics of the magnetic field, and wherein the analysis system is configured to determine spatial distribution of the nanoparticles from the spatial characteristics of the magnetic field.

19. An apparatus as in claim 14, wherein the magnetic measurement system is configured to measure the decay of the magnetic field over a period of time.

* * * * *